United States Patent [19]

Davenport et al.

[11] Patent Number: 5,151,909
[45] Date of Patent: Sep. 29, 1992

[54] FREQUENCY DOUBLED SOLID STATE LASER HAVING PROGRAMMABLE PUMP POWER MODES AND METHOD FOR CONTROLLABLE LASERS

[75] Inventors: Scott A. Davenport, Montara; Mark V. Ortiz, San Jose; Linda Chen, Fremont; Dirk J. Kuizenga, Sunnyvale, all of Calif.

[73] Assignee: Laserscope, San Jose, Calif.

[21] Appl. No.: 689,356

[22] Filed: Apr. 22, 1991

Related U.S. Application Data

[63] Continuation-in-part of Ser. No. 598,485, Oct. 16, 1990, abandoned.

[51] Int. Cl.[5] .............................................. H01S 3/10
[52] U.S. Cl. ........................................ 372/22; 372/21; 372/23; 372/25; 372/26; 372/10; 372/13; 359/326; 359/328
[58] Field of Search ............... 372/22, 21, 10, 13, 372/23, 25, 26, 38; 359/326, 328

[56] References Cited

U.S. PATENT DOCUMENTS

| | | | |
|---|---|---|---|
| 4,337,442 | 6/1982 | Mauck | 372/13 |
| 4,489,415 | 12/1984 | Jones | 372/38 |
| 4,514,848 | 4/1985 | Witte et al. | 372/25 |
| 4,791,631 | 12/1988 | Baumert et al. | 372/22 |
| 4,887,270 | 12/1989 | Austin | 372/22 |
| 4,907,235 | 3/1990 | Kuizenga | 372/21 |
| 4,913,533 | 4/1990 | Kafka et al. | 372/22 |
| 4,930,901 | 6/1990 | Johnston et al. | 372/10 |
| 5,025,446 | 6/1991 | Kuizenga | 372/22 |
| 5,068,546 | 11/1991 | Hemmerich et al. | 372/22 |

FOREIGN PATENT DOCUMENTS

1018515 11/1989 U.S.S.R. .............................. 359/326

OTHER PUBLICATIONS

Carlson, D., "Dynamics of a Repetitively Pump-Pulsed Nd:YAG Laser", J. Appl. Phys., vol. 39, No. 9, Aug. 1968, pp. 4369-4374.

Cunningham, R., "Q-Switching: Choosing the Best Alternative", Lasers & Application, Mar. 1987, p. 75.

Holmes, L., "Lamp-Pumped Nd: YAG Lasers Move Toward Higher Performance", Laser Focus/Electro-Optics, Nov. 1987, pp. 78-85.

Kagan, J., et al., "Simultaneous Dual-Wavelengths, 1.32 $\mu$m/106 $\mu$m Medical Laser", Conference on Lasers & Electro-Optics, May 1988, Technical Digest Series, vol. 7.

Keren, E., et al., "Optimization of the Energy Output of Pulsed Lasers", J. Appl. Phys., 53(3), Mar. 1982, pp. 1373-1380.

Koechner, W., "Applied Optics", 9, Jun. 1970, pp. 1429-1434 & pp. 2548-2553.

Koechner, W., "Solid-State Laser Engineering", Springer-Verlag, Jan. 1988, 2d Ed., pp. 402-436 & p. 53.

(List continued on next page.)

Primary Examiner—Georgia Y. Epps
Attorney, Agent, or Firm—Fliesler, Dubb, Meyer & Lovejoy

[57] ABSTRACT

A laser system using non-linear crystals for second harmonic generation and solid state gain media is operated under data processor control so that a plurality of pump power modes are available. The data processor modulates the pump power in a low power mode, and supplies continuous pump power in combination with Q-switching in a high power mode. Alternatively, modulation may be used in both low power and high power modes, with the parameters of the modulation adjusted under program control. Second harmonic generation without a Q-switch in high power modes can be achieved as well. The data processing control of pump power allows optimization of pump energy consumption and the generation of waste heat so that the laser resonator may be air-cooled in many environments. Also other design objectives can be achieved for specific laser applications using the program controlled data processor to drive the pump power source.

101 Claims, 16 Drawing Sheets

OTHER PUBLICATIONS

Kurobori, T., et al., "Q-Switching of ACW-Pumped Ng:YAG Laser with an LiF:$F_2$-μ Crystal", Optics Communications, vol. 58, No. 6, Jul. 1986, pp. 409-412.

Lotem, H., et al., "A 2 μm Holmium Laser", IEEE Journal of Quantum Electronics, vol. 24, No. 6, Jun. 1988, pp. 1193-1200.

Paunonen, M., "Air-Cooled Simmered Q-Switched Nd:YAG Laser with Transistor-Gated Flashlamp Pulsing", Conference on Lasers & Electro-Optics, OSA-/IEEE, Jun. 1984, Digest of Technical Papers.

Perkins, P. E. and T. S. Fahlen, JOSA, 4, Jul. 1987, pp. 1066-1071.

Roux, R., "French Develop 'Four-In-One' PDT Laser", Laser Focus World, Mar. 1990, pp. 95-96.

Shen, Y. R., "The Principles of Non-Linear Optics", John Wiley & Sons, Jan. 1984, p. 86.

Teichmann, H., et al., "Efficient Flashlamp-Pumped Operation of a Cr:Tm:Ho:YAG Laser at 2.08 μm", Conference on Lasers and Electro-Optics, Apr. 1988, Technical Digest Series, vol. 7.

Uppal, J., et al., "Study of Thermally Induced Active Birefringence in ND: Glass Laser Rods", J. Appl. Phys., 54(11), Nov. 1983, pp. 6615-6619.

Wall, K., et al., "Second Harmonic Generation Using a Long-Pulse Nd:YAG Laser", Conference on Lasers & Electro-Optics, OSA/IEEE Apr.-May 1987, Digest of Technical Papers.

Yao, J. Q., et al., "High Power Green Laser by Intracavity Frequency Doubling with KTP Crystal", High Power Solid State Lasers, SPIE, Jun. 1988, vol. 1021, p. 181.

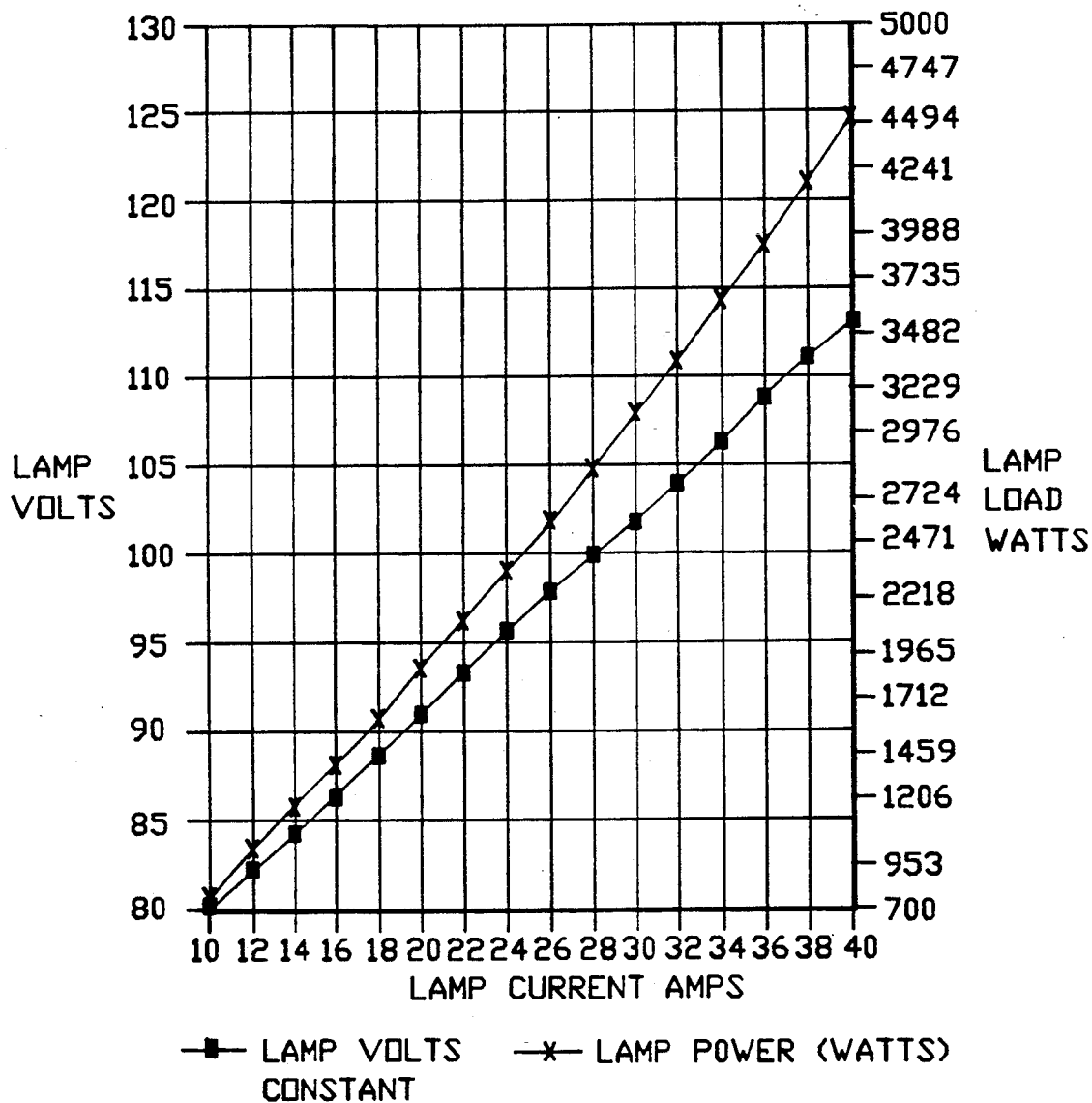
FIG.—3A

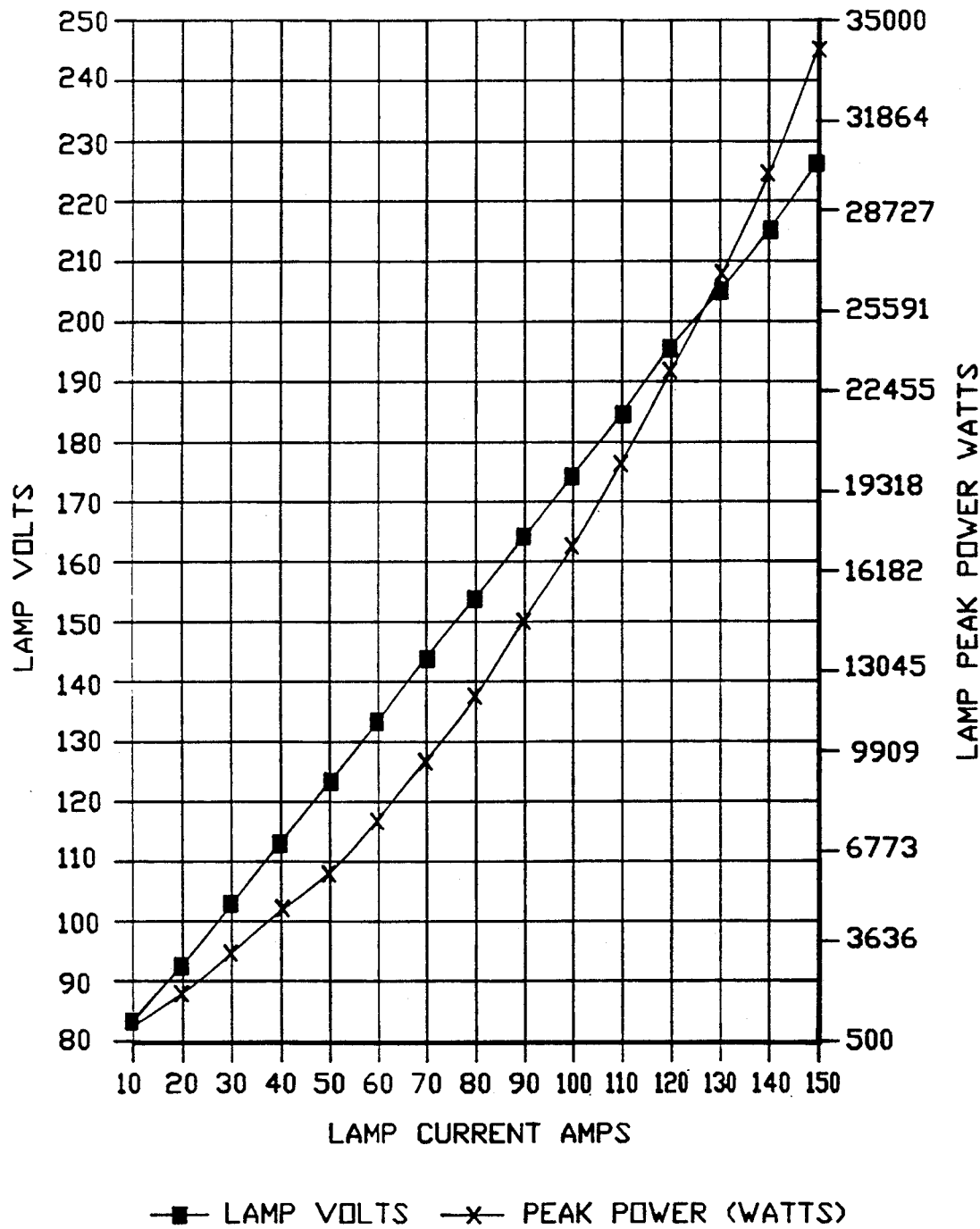
FIG.—3B

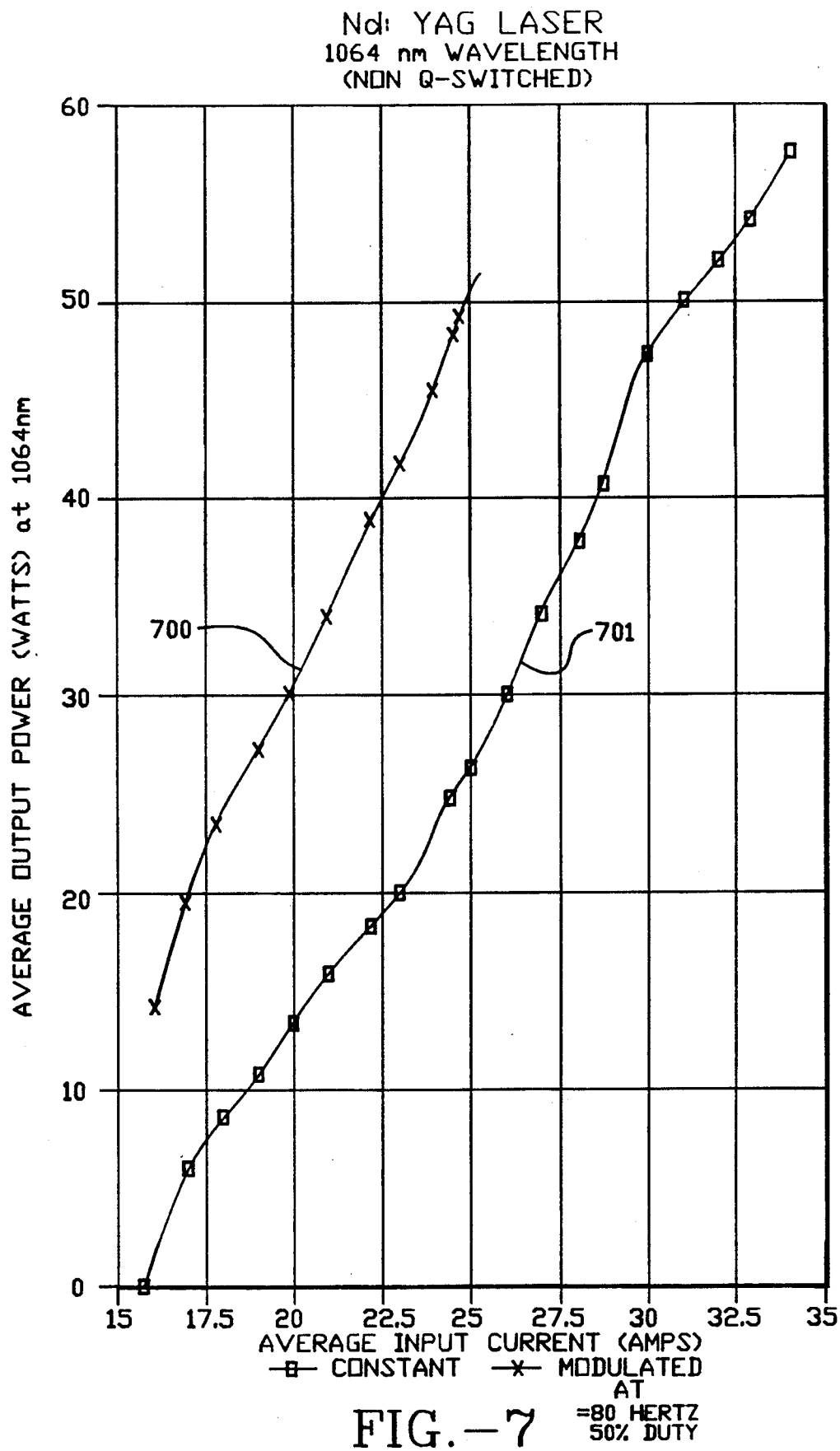
FIG.—7

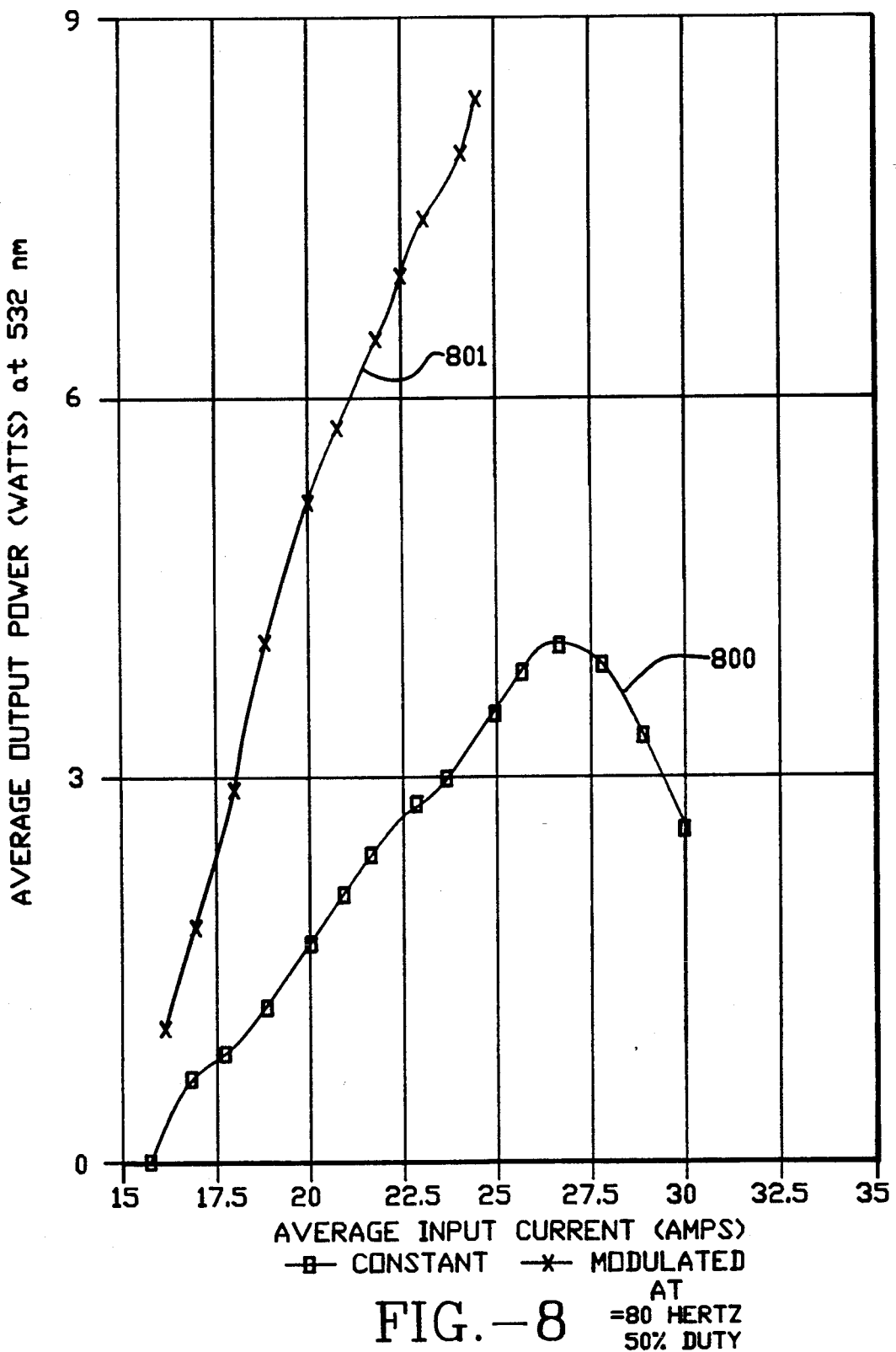
FIG.—8

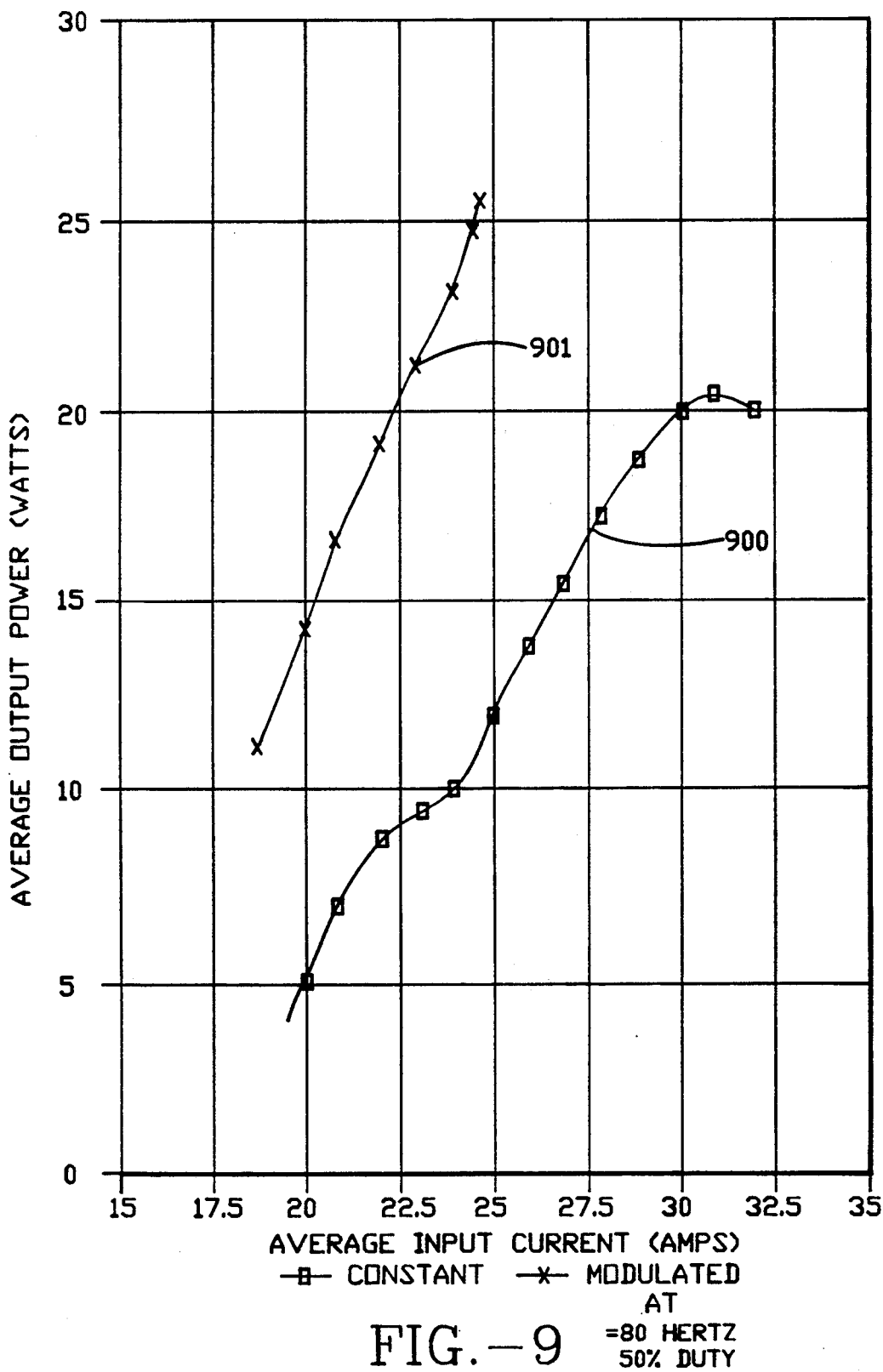

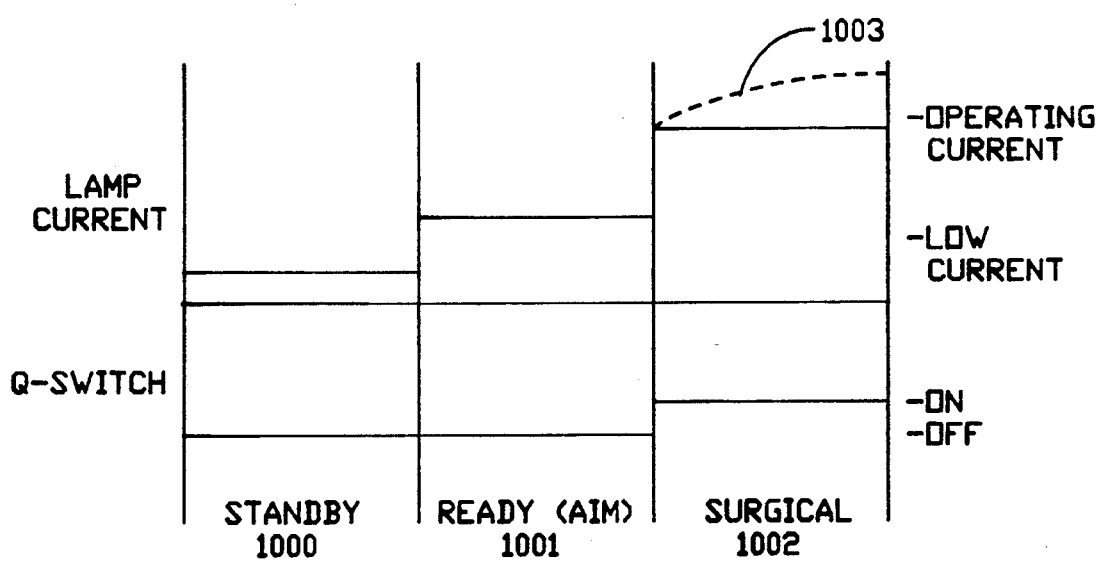
FIG.—10A
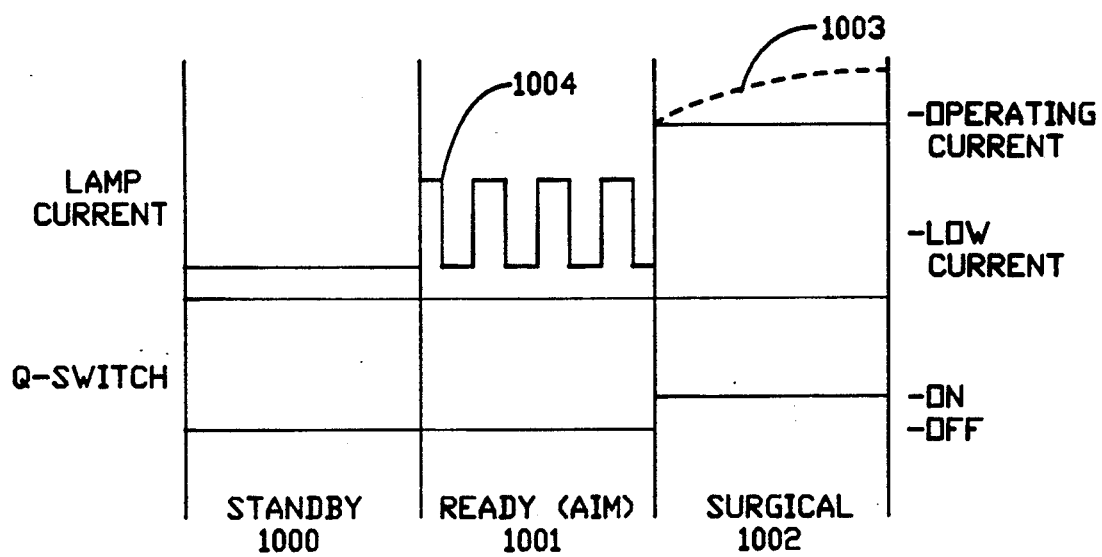
FIG.—10B

FREQUENCY DOUBLED SOLID STATE LASER HAVING PROGRAMMABLE PUMP POWER MODES AND METHOD FOR CONTROLLABLE LASERS

CONTINUING APPLICATION DATA

The present application is a continuation-in-part of U.S. patent application Ser. No. 07/598,485, filed Oct. 16, 1990, entitled AIR COOLING OF FREQUENCY DOUBLED SOLID STATE LASER FOR SURGICAL APPLICATIONS, now abandoned.

LIMITED COPYRIGHT WAIVER

A portion of the disclosure of this patent document contains material to which the claim of copyright protection is made. The copyright owner has no objection to the facsimile reproduction by any person of the patent document or the patent disclosure, as it appears in the U.S. Patent and Trademark Office file or records, but reserves all other rights whatsoever.

BACKGROUND OF THE INVENTION

1. Field of the Invention

This invention relates to laser systems, such as a frequency doubled Nd:YAG laser, operable in multiple pump power modes, and to such laser systems wherein the average power consumption of the laser is reduced so that the laser an be air-cooled while the average output power from the laser is maintained at or increased over the average output power of a conventional laser.

2. Description of the Prior Art

Lasers are now commonly used for a variety of medical, surgical, and industrial applications. Several types of solid state lasers are used in these applications, such as the Nd:YAG laser with a primary wavelength of 1064 nm in the near infrared. Also, such systems have been used with a non-linear crystal (such as a potassium titanylphosphate (KTP) crystal) inside the laser resonator, with output coupling devices designed to extract an output beam at a frequency, such as a second harmonic, derived from resonating beam. One useful system uses this technique to generate a green 532 nm output with a 1064 nm Nd:YAG laser. Typically, such Nd:YAG laser systems with a non-linear crystal, have a Q-switch to improve the conversion efficiency from 1064 nm to 532 nm.

A prior art surgical laser system produces an output beam with about 20W output power at 532 nm, which output beam is delivered to a patient's tissue through an optical fiber or other delivery system. The main advantage of the 532 nm wavelength is that it is strongly absorbed by the hemoglobin in blood and hence useful for cutting, vaporizing, and coagulating vascular tissue. Such a high power, frequency doubled Nd:YAG laser suitable for such uses is described by P. E. Perkins and T. S. Fahlen in JOSA, 4, pp. 1066–1071 (1987), and further improvements are described in U.S. Pat. No. 4,907,235, issued to Dirk J. Kuizenga on Mar. 6, 1990.

A surgical laser system typically has three modes of operation, called for identification herein, the standby mode, the ready mode, and the work mode. The laser goes to the standby mode, with no output power coming out of the system, when it is first turned on. Typically, the laser is in standby mode while the operating room is prepared and, in some cases, the laser can be in the standby mode for several hours. In this mode, the pump energy source, such as an arc lamp, may be turned on but operated below the laser threshold to warm up the pump energy source and prepare the system for an application of the work beam.

The ready mode is used to prepare the system for a fast transition to the work mode. In this ready mode, the pump energy source is driven well above laser threshold at or near the full power to be used in the work mode, to thermally stabilize the laser, so that on transition to the work mode, no undesirable transients in laser operation occur. Also, an aim beam is generated for aiming the work beam.

In a prior art frequency double Nd:YAG system, the laser gain medium is pumped at a high power during the ready mode, to generate a stable beam. The aim beam in such system is then produced by attenuating the laser output. For instance, the aim beam is obtained in a prior art frequency doubled Nd:YAG system by attenuating a laser output beam to less than 4 mW, at which the second harmonic beam is very clearly visible on vascular tissue, but not effective otherwise. Alternative ways to generate an aim beam include using other visible lasers, like a He-Ne laser at 633 nm, visible diode lasers at other wavelengths, or in some systems, using a white light incoherent source, which can be switched into the beam delivery system.

In the work mode full laser power is available to either cut, coagulate, or vaporize the target tissue. The system operator sets the required output from the laser for a typical application. In a typical system, output power can be adjusted from 50 mW to 20W.

The frequency doubled laser should switch from the ready mode to the work mode upon demand. For instance, in a surgical application, when the surgeon steps on a footswitch while aiming the beam to enable the work mode, the surgeon expects that the work mode laser output will be achieved immediately. A perceptible delay due to transients in the laser is not acceptable. Delay of more than the reaction time of the surgeon, 500 milliseconds for example, may make it difficult to insure that the work will be accomplished at the place identified by the aim beam before the switch is thrown.

The thermal effects of pumping the laser gain medium in many systems determine, to a large degree, the parameters of the ready and work modes. For instance, with Nd:YAG and other solid state gain media, thermal focusing is of concern. The pump power source, such as an arc lamp, pumps energy into the gain medium rod almost uniformly. The rod is cooled with water on the outside surface and consequently a thermal gradient is induced in the rod, with the maximum temperature at the center of the rod and lowest temperature at the outside surface where it is in contact with the water. This temperature gradient produces a thermal lens in many solid state media, and the dependance of the focal length of this lens on the laser pump power complicates the design of the laser. Thermal focusing is described in detail by W. Koechner in Applied Optics. 9, pp. 1429–1434, and pp. 2548–2553 (1970). U.S. Pat. No. 4,907,235 also discusses the design of the laser with thermal focusing. Two significant aspects of thermal focusing should be considered: first, these lasers are designed to have a stable optical resonator over a limited range of thermal focusing. At the low level end of pumping, the laser has weak thermal focusing and this may mean that the laser resonator is not stable. In that case, some minimum amount of pump power (possibly significantly higher than the theoretical laser threshold) is required to provide sufficient thermal focusing to make the resonator stable. In general, this means that more pump power has to be used to get stable and reliable output from the laser. Second, in a typical system, when the pump source is turned on rapidly from a very low level to the full power level required for stable laser operation, it takes from a fraction of a second to a few seconds to reach stable thermal conditions in the laser. During this time the output power from the laser may be erratic.

Another thermal property of Nd:YAG and some other solid-state laser materials is that the gain decreases as the temperature of the laser material increases. In a typical Nd:YAG laser system, for example, the output power starts to drop significantly due to this drop in gain as the laser cooling water temperature goes above 80 to 90° F.

U.S. Pat. No. 4,907,235 discloses a frequency doubled laser having a region of stability where the laser is Q-switched at 25 kHz (40 μs between pulses). In this laser, the ratio of spotsizes in the Nd:YAG medium to the non-linear crystal is about 2.5, and the laser must be pumped well above threshold with an electrical pump power of about 3 to 4 kW. Thus, the laser must be operated well above threshold all the time to get stable frequency doubled output.

Also, in prior systems, the output of the laser using non-linear crystals cannot be adjusted over a wide enough range for surgical applications by changing the pump power, such as by changing current through the arc lamp of the laser. An external laser beam attenuator is required to adjust the laser output to the range required for surgical applications. This is very different from the Nd:YAG lasers without non-linear crystals and without Q-switching, in which the output is adjustable directly with the pump power.

Other components of frequency doubled systems are also involved in the resonator design. The non-linear crystal (e.g., KTP crystal) used for frequency doubling has non-linear behavior such that the output power at the second harmonic increases with the square of the input power at the fundamental frequency, or $$P_2 = kP_1^2$$

Where
$P_2$ = Power at second harmonic (532 nm)
$P_1$ = Power at fundamental (1064 nm)
k = constant of proportionality.

This is described in several standard text books such as *The Principles of Non-Linear Optics* by Y. R. Shen, John Wiley & Sons, 1984, p. 86. The above equation is correct as long as the total conversion from fundamental to second harmonic remains small, typically less than 20 to 30%. The significance of the non-linear behavior becomes very important when the fundamental power is being pulsed. Consider the simple example where the fundamental power is pulsed at a 50% duty cycle and the average fundamental power remains the same. For the 50% of the time that the fundamental power is turned on, the peak power is near twice the average to maintain a constant average power. The second harmonic generation increases to four times the power that it would be with a constant fundamental input power, and for the 50% duty cycle, the average second harmonic power is increased by a factor of two. This relationship can easily be extended to show that for a duty cycle of K (fraction of the time the power is turned on) and with the average pump power the same, the average second harmonic increases by 1/K. Thus, for a 20% duty cycle, the increase in average second harmonic power is 5 times over a constant pump power at the same average power. This property of second harmonic generation becomes very significant when the laser is being pulsed.

A second essential component to consider is the Q-switch with its inherent instabilities. Repetitive Q-switching of an Nd:YAG laser is described in several standard texts such as *Solid-State Laser Engineering* by W. Koechner, Springer-Verlag, 1988, Second Edition, pp. 402-436. When high average output power is required, the laser is Q-switched at a high repetition rate. However, if the repetition rate is too high, an instability sets in. Instead of producing a train of pulses that are all equal, the laser begins operating so that every second pulse is much smaller. In essence, the large pulses extract all the energy from the laser medium, and when the laser is Q-switched after a large pulse, not enough energy has been stored for the next pulse, and the next pulse is small. The behavior of the laser in this mode becomes more erratic and the high intensity of the large pulses can damage some optical components inside the laser resonator.

Doing simultaneous intracavity second harmonic generation with Q-switching has some advantages. The non-linear behavior of the second harmonic generation (SHG) described earlier will increase the conversion to the second harmonic power at the peak of the large pulses. This SHG non-linearity will thus counteract the Q-switching instability by reducing the amplitude of the larger pulses and equalizing the pulses. However, should the SHG crystal be misaligned and phasematching lost, the large pulses associated with Q-switching will occur and can damage the SHG crystal.

In addition, many elements of a laser system have characteristics that change over time. For instance, an arc lamp ages such that it takes a higher input current to deliver a given output pumping power. Similar aging occurs with other parts of the laser system, such as the gain medium, or other elements that may be in the beam path inside or outside the laser cavity. Thus, in prior art laser systems, adjustments are made at the factory which set a desired input current for driving arc lamp pump sources, using potentiometers or the like, in order to deliver the desired output power. However, as the arc lamp, or other elements of the laser system age, the output power will decrease for that given input current. Since the user cannot adjust that preset current, the laser system suffers a degradation in performance over time.

One technique which is used to monitor the aging of laser systems is to store an output power log in the control system for the laser. This log can then be accessed by service personnel. Based on this stored output power log, the service personnel can make certain assumptions useful in diagnosing problems with the system.

However, the stored output power log used for diagnosis of laser system problems, is a limited information set because of the preset input current to the pump power source.

All the above considerations influence the design of the frequency-doubled laser. For example, in a laser with a Nd:YAG rod 4.0 mm in diameter, 3" long, pumped by a Krypton arc lamp with 6 mm inside diameter and 3" arc length, a KTP crystal 3 mm by 3 mm and 5 mm long, with a spotsize 2.5 times smaller than the spotsize in the Nd:YAG rod, an acousto-optic Q-switch operating at 25 kHz 24W of laser output power at 532 nm may be produced. Pump power required to get this laser output power is about 3.0 to 4.0 kW, and the pump power must stay at this level in both the ready and work modes of operation. The laser design for frequency doubling depends on the thermal focusing produced to keep the laser resonator stable. All thermal transients that may affect stability are avoided by keeping the pump power at full power in both modes. The aim beam during the ready mode is produced by attenuating the full power beam from the laser. To maintain this high pump power, with the attendant waste heat, the laser and particularly the gain medium Nd:YAG rod and krypton (Kr) arc lamp must be cooled with an internal closed-cycle water recycling system, with a water-to-water heat exchanger that is connected to an external water source for cooling. The closed loop system maintains the water clean and pure enough to cool the laser without contaminating the arc lamp or Nd:YAG rod. Typically, 1½ to 2 gallons per minute are required from the external source at more than 30 psi to remove the waste heat, which in this example can be as much as 4 kW.

As described above, Q-switching the fundamental input power to the non-linear crystal can increase the average second harmonic power produced. Yao, J. Q., et al., "High Power Green Laser by Intracavity Frequency Doubling with KTP Crystal", published in *High Power Solid State Lasers* (1988), SPIE, Vol. 1021, p. 181, describes another way of increasing the average second harmonic power for a given average pump power; that is to pulse the lamp that pumps the Nd:YAG rod in combination with the Q-switching. Yao, et al. disclose a theoretical and experimental study on a KTP frequency doubled Nd:YAG laser which increases the second harmonic laser output power by "Quasi-CW Pumping". Quasi-CW pumping is described as having a repetition rate of 5 to 100 Hz. Parameters such as minimum current, maximum current, and specific applications are not disclosed or suggested.

Many conventional laser systems which do not have to address the complication of frequency doubling, particularly the Nd:YAG laser systems with output at 1064 nm, have replaced the water-to-water heat exchanger with a water-to-air heat exchanger and are referred to as air-cooled lasers. In surgical use, the conventional air-cooled laser is never turned on at high pump power continuously for a long period of time. Moreover, in systems where the laser goes to high power (and high pump power) only on demand when the surgeon "steps on the footswitch", the *average* thermal load is not very large. With a reasonable sized water reservoir and water-to-air heat exchanger, these systems can be successfully air-cooled. The advantages of air-cooling are many: 1) no costly water installation in the operating room is required, 2) no inconvenient water hook-ups, 3) the system is much more mobile from operating room to operating room, and 4) power consumption of the system is lower. It is thus extremely desirable to produce a system with second harmonic generation ("SHG") that can be air-cooled. As can be seen from the above discussion, it is desirable to provide a frequency doubled laser system capable of operation in a variety of output modes to optimize performance for a variety of applications of the output beam, and to minimize waste heat.

SUMMARY OF THE INVENTION

The present invention provides a laser system using non-linear crystals for extracting second harmonic frequencies or other frequencies derived from the resonating frequency in the laser, characterized by multiple modes for delivering pump power to the gain medium. The modes include at least a low power mode, such as a ready mode, and a high power mode, such as a work mode, for accomplishing work with the laser beam. Using the multiple pump power modes, the laser system can be optimized to achieve many desirable results, including minimizing waste heat generated so that air cooling systems can be used with the laser system.

Thus, according to one aspect of the present invention, a laser resonator is provided for resonating at a first frequency which includes a solid state gain medium. A controllable pump power source is coupled with the gain medium which is responsive to at least one control signal for supplying pump power to induce laser gain. A non-linear crystal, and an output coupler are provided with the laser resonator for extracting an output beam at a second frequency derived from the first resonating frequency, such as a second harmonic. A control circuit is connected to the controllable pump power source, for supplying at least one control signal to control the output power of the output beam, by controlling the controllable pump power source. The control circuit supplies the control signal in a first mode to generate a low output power, such as may be used for the ready mode, and in a second mode to generate a high output power, such as may be used for accomplishing work with the beam.

The control circuit, according to one aspect of the invention, is a programmable data processor. The programmable data processor is able to configure the pump power mode in a variety of fashions to achieve a desired output power. In one aspect in a low power mode for generating a second harmonic output, the pump power is modulated, so that a low average pump power generates sufficient frequency doubled output for the low power objectives and to stabilize the resonator. Thus, according to this aspect, the controllable pump power source includes a power supply for generating an electric power signal having characteristics specified by the control signals from the data processing system. A transducer, such as an arc lamp, is provided for transducing the electric power signal into pump power, according to the characteristics of the electric power signal. The data processor supplies the control signals in the low power mode to generate a modulated pump power with a selectable average pump power and selectable peak pump power. The data processing system can control these parameters using feedback from an output power detector, or calibration techniques, such as by generating and storing an output power versus input current table for the particular modulation frequency and duty cycle, and setting the pump power according to the calibration table.

According to another aspect of the invention, the laser resonator includes a Q-switch, which is utilized in the high power mode. Thus, the data processor can control the laser system further by controlling Q-switching parameters. In the high power mode, the pump power can be modulated or unmodulated, with or without Q-switching.

In other aspects of the invention, the control circuitry supplies control signals to the pump power source during transitions from the low power mode to the high power mode, so that the output power does not overshoot a selected high output power during transition by more than a predetermined maximum amount, and so that the transition occurs quickly.

According to yet another aspect of the invention, a laser system is provided which includes a laser resonator as described above, coupled with a beam delivery system, such as a fiber-optic cable used for delivering an output beam to a work site. Also, the user of the system will have an input switch by which data can be input to the data processor. In the low power mode, the beam is delivered through the fiber-optic delivery system for aiming the beam without affecting the work site. When the user depresses a switch on the input device, the data processing system immediately causes a change in pump mode and an increase in the output power to achieve work. This output power increase is achieved without perceptible delay, or in less than 100 to 200 ms, so that any movement of the fiber-optic delivery system while waiting for the transition is minimal.

In other embodiments, a detector is coupled with the delivery system for supplying measurements of the output power to the data processor. An input panel is provided by which the user can set a desired low output power and a desired high output power for the respective modes. The data processor controls the pump power source during a calibration mode to determine parameters based on pump power versus output power measurements in the low power and high power modes of operation. These laser parameters are utilized together with the input supplied by the user to control the pump power source during actual operation of the system.

According to another characterization of the invention, the laser resonator as described above, is provided with an air-cooling system which dissipates a limited amount of waste heat into air surrounding the laser system. The control means operates the laser during the low power mode with modulated pump power and during a high power mode to accomplish work, so that the average pump power remains low enough during normal operation of the system that the waste heat generated by the laser system remains less than the limited amount of waste heat that can be dissipated by the air-cooling system.

According to yet another aspect of the present invention, the laser resonator comprises a Nd:YAG gain medium and a KTP non-linear crystal for generating a 532 nm output used in surgical applications. The low power mode is used for aiming the beam with a fiber-optic delivery system. The high power is used for accomplishing work on a patient.

Furthermore, the data processing system is capable of operating the laser system in a standby mode in which the pump power supply, such as an arc lamp, is maintained on but below laser threshold so that no output beam is generated. This allows a transition from a standby mode to the low power mode very quickly by reducing the amount of time it takes the pump power source to stabilize when it is turned on.

A method is presented for operating a laser system including a laser medium and a non-linear crystal within a laser resonator, wherein the non-linear crystal provides conversion of an oscillating mode to a desired output frequency, and including a controllable means for energizing the laser medium. The method comprises:

controlling the energizing means in a work mode to supply sufficient power to the laser medium to generate a work mode output beam having a desired power from the laser resonator;

controlling the energizing means in a ready mode to supply sufficient power to the laser medium to thermally stabilize the laser resonator above laser threshold for efficient conversion by the non linear crystal to generate ready mode output beam from the laser resonator, wherein average power supplied by the energizing means during the ready mode is less than average power supplied by the energizing means during the work mode;

controlling the energizing means during transitions from the ready mode to the work mode, so that the transitions occur without unacceptably long delay relative to user's reaction time.

The laser system in one preferred embodiment further includes components sensitive to overshoot of the desired output power of more than a determinant amount, and the step of controlling the energizing means during transitions includes preventing overshoot of the desired output power, by more than the determinant amount.

The laser system in another preferred embodiment further includes a cooling sub-system dissipating up to determinant amount of waste heat into air surrounding the laser system, and the steps of controlling the energizing means in the ready and work modes results in average generation of waste heat of less than the determinant amount.

The present invention provides, in yet another aspect, a method for operating a laser system including a laser medium within a laser resonator for generating an output beam, the laser system also including a controllable means for energizing the laser medium and a detector for indicating power of the output beam. The method comprises:

controlling the energizing means in a characterization mode to characterize power of the output beam relative to power supplied to the energizing means for one or more modes of operation of the laser system; and controlling the energizing means in the respective nodes in response to the characterization to supply sufficient power to the laser medium to generate output beams having desired powers from the laser resonator for the one or more nodes.

The present invention is particularly useful for generating the green output beam using a Nd:YAG laser for surgical applications. The system allows consistent operation of the laser because of the calibration mode as the characteristics of a pump lamp or other pump power source change with age. The system generates minimal waste heat and can be used in conjunction with air-cooling so that no expensive plumbing is needed in the operating room to provide the cooling water. The system allows use of a single laser resonator to provide the aim beam with the resonator providing the work beam, which can reduce the costs and complexity of the laser system. All of these advantages contribute to making surgical techniques using lasers less expensive and available in more places.

Other aspects and advantages of the present invention can be seen upon review of the figures, the detailed description, and the claims which follow.

BRIEF DESCRIPTION OF THE DRAWINGS

FIGS. 3a and 3b show the voltage/current characteristic of a typical krypton arc lamp for CW and pulsed operation, as supplied by the manufacturer of the lamp.

FIG. 7 shows the average output at 1064 nm of a typical Nd:YAG laser with and without pump current modulation as a function of average lamp current.

FIG. 8 shows the average output power for a non Q-switched frequency doubled Nd:YAG laser at 532 nm with and without pump current modulation as a function of average current into the arc lamp.

FIG. 9 shows the average output power for a Q-switched, frequency doubled Nd:YAG laser at 532 nm with and without pump current modulation as a function of average current into the arc lamp.

FIG. 10a shows the lamp current waveform and Q-switch control signals during standby, ready, and work modes for one embodiment of the invention.

FIG. 10b shows the lamp current waveform and Q-switch control during standby, ready, and work modes according to another embodiment of the invention.

DETAILED DESCRIPTION OF THE INVENTION

Figure 1:
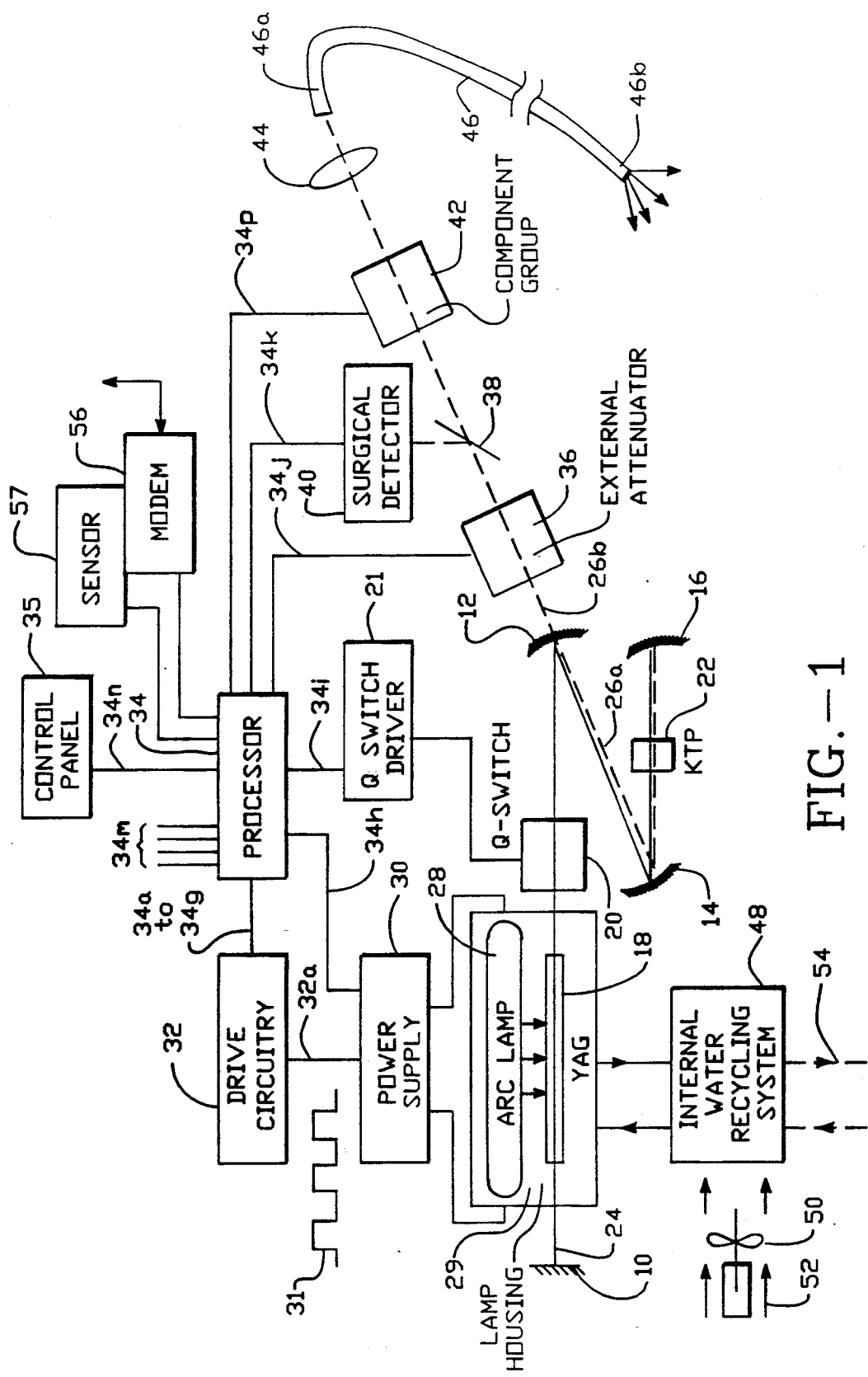
FIG. 1 is a general block diagram of the laser system embodying the present invention.

Preferred embodiments of the present invention are described with reference to the figures. FIG. 1 shows a block diagram of a preferred laser system according to the present invention. In FIG. 1, a laser resonator is defined by end mirror 10, turning mirrors 12 and 14, and end mirror 16. All of these mirrors are high reflecting (greater than 99.8 %) at the 1064 nm line. An optical path 24 is defined by these mirrors. A gain medium 18 comprising a Nd:YAG rod is mounted along the optical path within a lamp housing 29. An arc lamp 28 is also mounted within the housing and supplies pump power to the gain medium in response to current generated in power supply 30. Also in the optical path 24 is a Q-switch 20 between the lamp housing 29 and the turning mirror 12. A non-linear crystal 22 is mounted between the turning mirror 14 and the back mirror 16. This non-linear crystal is preferably a KTP crystal aligned for frequency doubling to generate a 532 nm beam. Mirrors 16 and 14 are highly reflective at 532 nm, while mirror 12 is transmissive and operates as an output coupler for the 532 nm beam.

This basic resonator design is described in detail in U.S. Pat. No. 4,907,235, invented by Kuizenga, which is hereby incorporated by reference for background information and for description of the laser resonator parameters.

Thus, the laser resonator is designed for resonating at a first frequency, i.e., 1064 nm along the Z-shaped optical path 24. A second frequency derived from the 1064 nm beam is generated in the KTP crystal 22. This beam travels along the path 26a and is extracted from the resonator to supply an output beam along path 26b.

The output beam along path 26b passes through a controllable attenuator 36, a beam splitter 38, which supplies a portion of the output beam to a surgical detector 40, and a component group 42 as described in more detail below. The attenuator, detector, and component group are all coupled to a data processing system 34, across lines 34j, 34k, and 34p.

The Q-switch 20 is controlled by Q-switch driver 21, which is, in turn, coupled to data processor 34 across line 34i. In the preferred system, the Q-switch is an acoustic-optic Q-switch.

Similarly, the power supply 30 generates an electrical power signal for controlling the arc lamp 28. This power signal is controlled by the data processor 34 across line 34h and by drive circuitry 32 across line 32a. Drive circuitry 32a is controlled by the data processor across lines 34a through 34g. A sensor 57 is coupled with the data processor to sense an environmental condition, such as temperature or humidity, that affects operation of the laser system. A modem 56 is connected to the data processor 34, providing an interface for remote access to memory in the data processor. Finally, a control panel 35, by which a user can supply input signals and parameters, is provided. This control panel 35 is connected to the data processor 34 across line 34n.

In alternative systems, the non-linear crystal may be mounted outside the resonant cavity of the resonator. Also, it may be used for extracting outputs other than the second harmonic, such as sum-of-frequency derivation or the like.

In one preferred system, the data processor 34 consists of an Intel 80186 microprocessor mounted on a main control PC board in the laser system, including various peripheral circuits, such as analog-to-digital converters (ADC), drive circuits, memory devices, and other peripherals, as known in the art, to form a data processing system which operates under program control.

The program controlled data processor 34 in turn generates control signals for controlling the drive circuitry 32 and pump power supply 30 to specify pumping modes of the laser system. Also, the program controlled data processor 34 controls the Q-switch 21 and the components in the beam path outside the laser resonator. The surgical detector 40 and other detectors in the component group 42 provides the data processor 34 with measurements of the output power which can be used to accomplish a closed loop control system, or during calibration to determine pump mode versus output power parameters, as explained in more detail below.

In the preferred system, the mirror 12 has a radius of curvature of 50 cm and mirror 14 has a radius of curvature of 20 cm to provide a 2.5 magnification relay of the beam at the output of the YAG rod 18 to the KTP crystal 22. The criticality of this relationship is described in detail in the above-referenced U.S. Pat. No. 4,907,235. The YAG rod 18 is 79 mm long and 4 mm in diameter. The KTP crystal 22 is 3 by 3 mm square and 5 mm long. Mirror 10 is a flat mirror, and mirror 16 has a radius of curvature of 10 cm. For a particular laser resonator design, the mirrors 10 and 16 determine the range of thermal focusing within which the resonator will be stable.

The pump power source is a krypton arc lamp, 3" long, with an internal diameter of 6 mm. Lamp is available from Q-Arc Co. of Cambridge, England. The arc lamp is powered by power supply 30, such as a YAG DRIVE Trademark 6 kW arc lamp power supply manufactured by A. L. E. Systems, Inc. Of Massachusetts. This power supply is particularly suited to the krypton arc lamp referred to above. In the preferred system, the external packaging of the power supply may be modified so that it physically fits within a laser cabinet. This power supply generates an electric power signal in the form of a current controlled by an input voltage from 0-5 V. The output current varies with the input voltage such that a 0.6 V input causes nominally a 6 amp output, while a 5 V input causes a 50 amp output. The power supply is a high frequency switching type power supply having a relatively fast output current response time, on the order of a fraction of a millisecond. When coupled with an arc lamp, the rise time is still quite fast, in the range of a millisecond. This rise time is fast enough that it makes it possible to modulate the lamp current at frequencies suitable for various pumping modes, as described below. The drive circuitry 32 is described below with reference to FIG. 4.

Of course, alternative pump power sources, such as laser diode arrays, other lasers for longitudinal pumping, and others, can be used as suits the needs of a particular gain medium and application of the laser system.

The lamp housing 29 in the embodiment of FIG. 1, as standard in the art, includes passages for flowing cooling water in contact with the Nd:YAG rod 18 and the arc lamp 28 for cooling of these components. Water supplied by an internal water recycling system 48, which includes a radiator fan 50 which drives air (schematically block 52) over the radiator to dissipate a limited amount of heat into the air surrounding the laser system. In one preferred system, heat is dissipated at about 600 W in the standby mode, 1-2 kW in the ready mode, and 2.54 kW in the work mode. However, the average amount of dissipated heat is less than the amount determined by the capabilities of the cooling system. As an alternative, as indicated by the lines 54, an external water cooling can be used for dissipating large quantities of heat.

Figure 2:
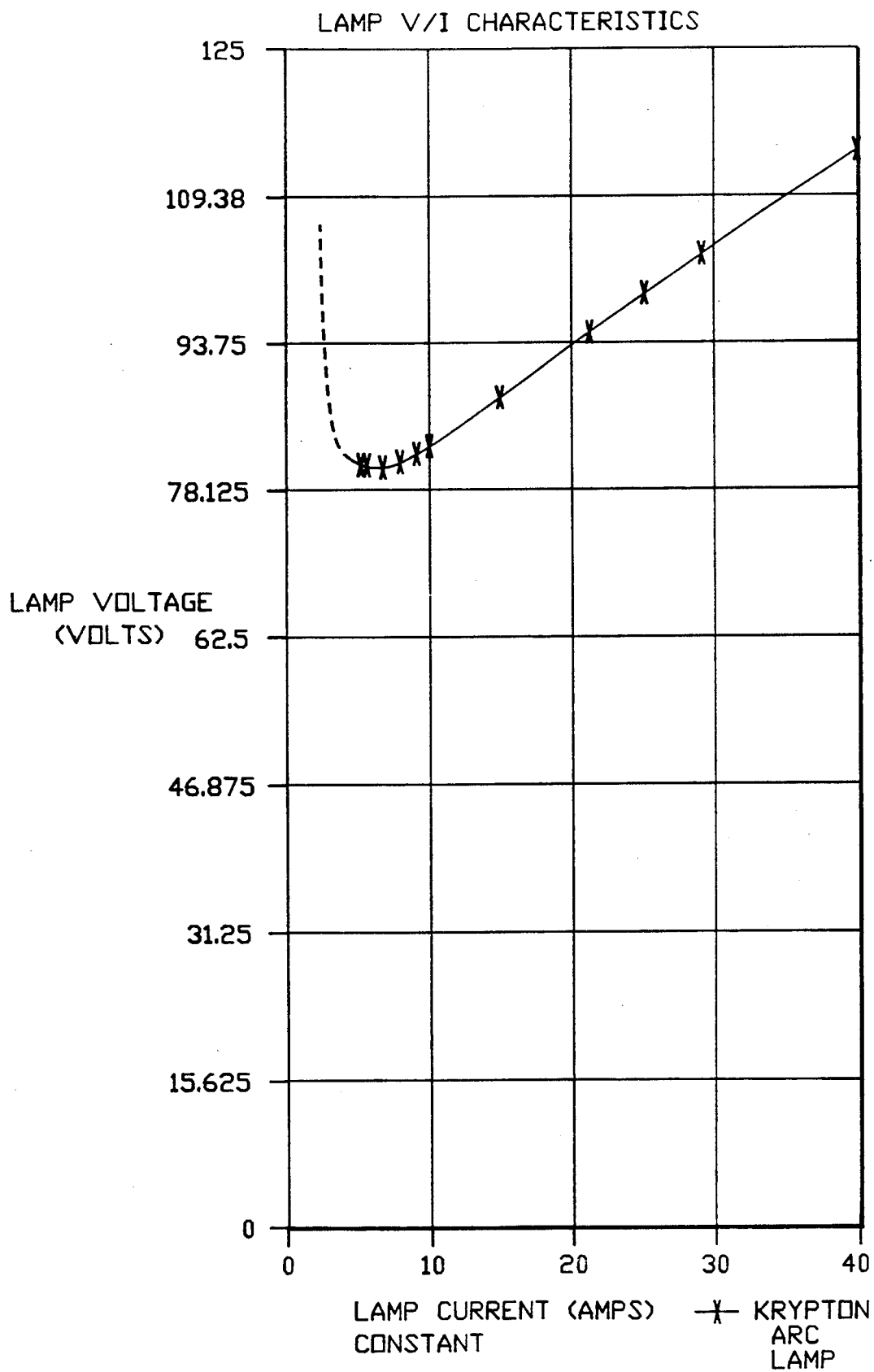
FIG. 2 shows the voltage/current characteristic of a typical krypton arc lamp for CW operation.

FIGS. 2, 3a, and 3b illustrate further characteristics of the arc lamp 28. FIG. 2 shows the voltage/current characteristic of the arc lamp 28. This lamp can be used with a constant current up to 40A. At that current level, the voltage is about 115 V, for a total power input of 4.6 kW. Note that at the low current level of about 6A, the voltage has a minimum level. Depending upon the power supply design used, operation below 6A for this lamp may require external ballast resistors. In the preferred embodiment of this invention, external ballast resistors are not used and the minimum simmer current for the lamp during the standby mode of the system is determined without them.

FIGS. 3a and 3b illustrate the arc lamp manufacturer's voltage/current plots for the krypton arc lamp used in the invention. FIG. 3a illustrates the voltage/current curve for constant current operation. FIG. 3b illustrates the voltage/current curve for pulsed operation. Peak currents up to 150A can be used, with peak powers into the arc lamp of 35 kW. However, the duty cycle into the lamp should be such that average input power remains below 5.0 kW. Note that the lamp is designed for constant current operation, and in pulsed operation the life of the lamp may be much shorter. Q-Arc Co. of England, produces pulsed lamps, but these lamps may not be stable enough for constant current operation. A lamp design which would operate in both constant and pulsed modes of operation might be advantageous and worth consideration.

Figure 4:
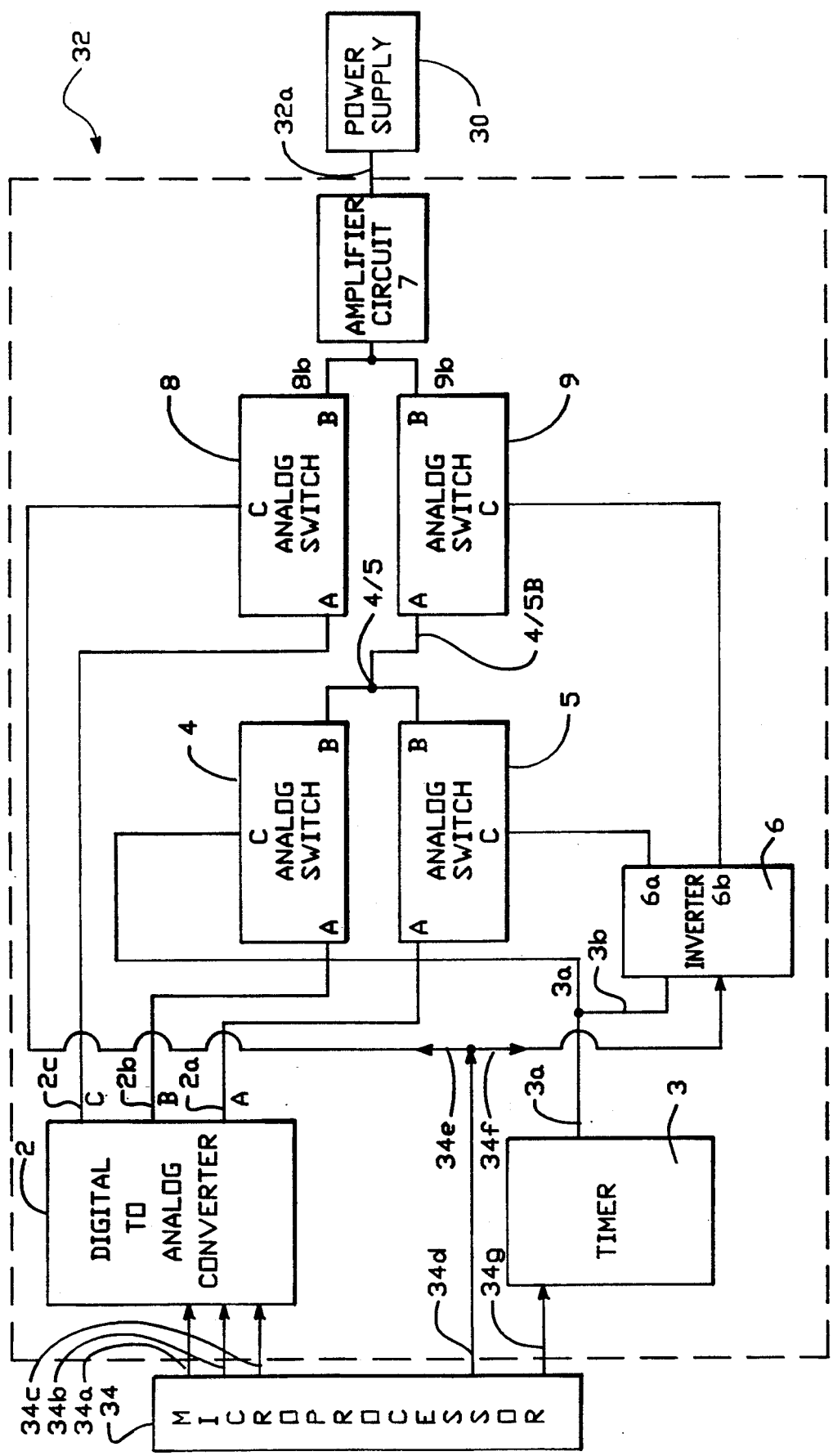
FIG. 4 is a schematic of the drive circuit for the lamp driver in the preferred embodiment of this invention.

The drive circuit 32 of FIG. 1 used in generating the pump power modes is illustrated in FIG. 4. This drive circuit is coupled to the data processor 34 across lines 34a, 34b, 34c, 34d, and 34g. The inputs 34a, 34b, 34c are coupled to digital-to-analog converter 2. The digital-to-analog converter 2 has outputs A on line 2a, B on line 2b, and C on line 2c. The input 34d is supplied across line 34e as a control input to analog switch 8, and across line 34f as an input to inverter 6. The input 34g is connected to timer 3. The output of the timer 3 is supplied on line 3a as a control input to analog switch 4 and across line 3b as an input to inverter 6.

The inverter 6 has an output 6a connected to the control input of analog switch 5 and an output 6b connected to the control input of analog switch 9.

Analog switch 4 and analog switch 5 have their inputs connected respectively to the B and A outputs of the digital-to-analog converter 2 across lines 2b and 2a. The outputs of analog switches 4 and 5 are coupled together at node 4/5 and as an input on line 4/5b to analog switch 9. The input to analog switch 8 is connected to the C output across line 2c from the digital-to-analog converter.

The outputs of analog switches 8 and 9 across lines 8b and 9b are connected together and as an input to amplifier 7. Amplifier 7 supplies an output on line 32a to the power supply 30, as illustrated in FIG. 1.

In operation, the data processor 34, in response to a program, loads the digital-to-analog converter with a channel A low modulation level cross lead 34a, a channel B high modulation level across lead 34b, and a channel C operational level across lead 34c. The user provides, through the input panel, parameters which identify the particular power level associated with standby, ready, and work modes (control panel 35). Alternatively, these levels can be preprogrammed in the data processor.

To generate a continuous pump mode, the control signal 34d is asserted high. This opens switch 8, and is supplied through inverter 6 to close switch 9. With switch 8 open, the channel C current value is supplied through the amplifier circuit 7 to the power supply 30. For a modulated pump power mode, the data processor sets the signal on line 34d low. This closes switch 8 and, by operation of inverter 6, opens switch 9. The modulation rate, which is set by the data processor across line 34g to timer 3, is then determined by the output of the timer on line 3a. This timer 3 alternatively opens switches 4 and 5 so that a low modulation current level from channel A through switch 5 is supplied during one half cycle to line 4/5b and a high modulation current level from channel B through switch 4 is supplied during the other half cycle. With switch 9 open, a square wave is supplied at output 9b through amplifier circuit 7 across line 32a to the power supply.

Obviously, a wide variety of other switching circuits could be implemented as suits the needs of a particular design.

The timer 3 is preferably an 8-bit programmable timer and is set to the desired frequency of modulation. As mentioned above, this is 83 Hz in the embodiments described with reference to FIG. 1. The output of the timer also controls the duty cycle of the modulated pump mode. In the preferred system, the duty cycle is 50% as mentioned above, but can be adapted as necessary for a given system.

In the system described with reference to FIG. 1, the low modulation level across channel A is scaled so that the output of the amplifier on line 32a is between 0.5 and 0.7 volts. The high modulation level is from 2.5 to 3.5 volts for use in the ready mode modulation. The operational level on channel C is set anywhere from 0.05 to 4.5 volts for use in either the standby mode, or to control the output power of the laser over a wide range.

The components used in the implementation of FIG. 4 include an analog devices AD7226DAC2; Intel 8254 timer 3; National Semiconductor 4066 analog switches 4, 5, 8, and 9; and a National Semiconductor 7406B inverter 6. Obviously, a wide variety of components can be used to implement this type of switching circuit.

According to the preferred embodiment invention, a frequency doubled solid-state laser is operated in the standby mode at low power levels, sometimes for a very long period of time (hours), such that the energy consumption of the laser is low. This can be done by setting the standby lamp current to preferably 6A with an average power into the laser of about 500 W. It is possible to lower the lamp current even further, to below 1A lamp current, so that there is less than 100 W average power into the laser system.

The lamp current value used in standby mode is too low to provide fast transition to full power in the work mode. Moreover, other unwanted transients such as overshoot of the output power at the start of the work mode can easily occur. With a few hundred watts into the lamp, the thermal load on the Nd:YAG rod is low and thermal focusing and other distortions have minimal effects. In many resonator designs, the resonator with this small amount of thermal focusing is unstable. At the start of the work mode, the lamp current can be increased to full power rapidly within a few to tens of milliseconds. The thermal focusing develops much slower, and it can take a fraction of a second to a few seconds for the Nd:YAG rod to heat up and develop sufficient focusing for the resonator to become stable and for the laser to go above threshold and deliver output power. At this stage the Nd:YAG rod is still cooler than it would be under steady state condition with full power loading. The gain is somewhat higher due to the cooler rod. However, the thermal distortion and losses due to this distortion are low, and yet the lamp current is at full power level. The laser power increases rapidly and can easily overshoot the power that the laser would produce under steady state conditions. This is a particularly difficult problem in a frequency doubled Nd:YAG laser because of the non-linear (quadratio) dependence of the second harmonic power on the fundamental power level in the laser. These problems make it very difficult to make the transition to full power at the start of the work mode when starting from a very low standby mode lamp current.

In the preferred system, the ready mode solves the problem with transition to full power in the work mode. During the ready mode an average lamp power is set at an intermediate level which is high enough so that the laser is above threshold at the start of the transition to the work mode. This means that the output power will increase immediately at the start of the work mode as the lamp current increases. The average lamp power according to the invention preferably ranges from 1-2 kW and depends on the laser design.

The level to which the lamp current is set at the start of the work mode also has to be chosen carefully so that the overshoot is minimized. At this lamp current level, the additional losses introduced into the resonator due to thermal distortions should not be very large. This will prevent large overshoot in the laser output power at the start of the work mode. The lamp current level at the start of the work mode preferably ranges from 15-25 amps and depends on the laser design.

The processor drives the laser in such a manner during the ready mode that the output from the laser at the second harmonic is stable enough to be useful as an aim beam. This condition can be met when the lamp current is modulated. The average power into the lamp is still at the level to achieve the objectives described above, and at the peak current during modulation, the laser is far enough above threshold to produce stable output power from the laser. During this time, the laser is not Q-switched because less power is required for the aim beam than the surgical beam. Any instability in the Q-switching dynamics is also avoided.

Figure 5:
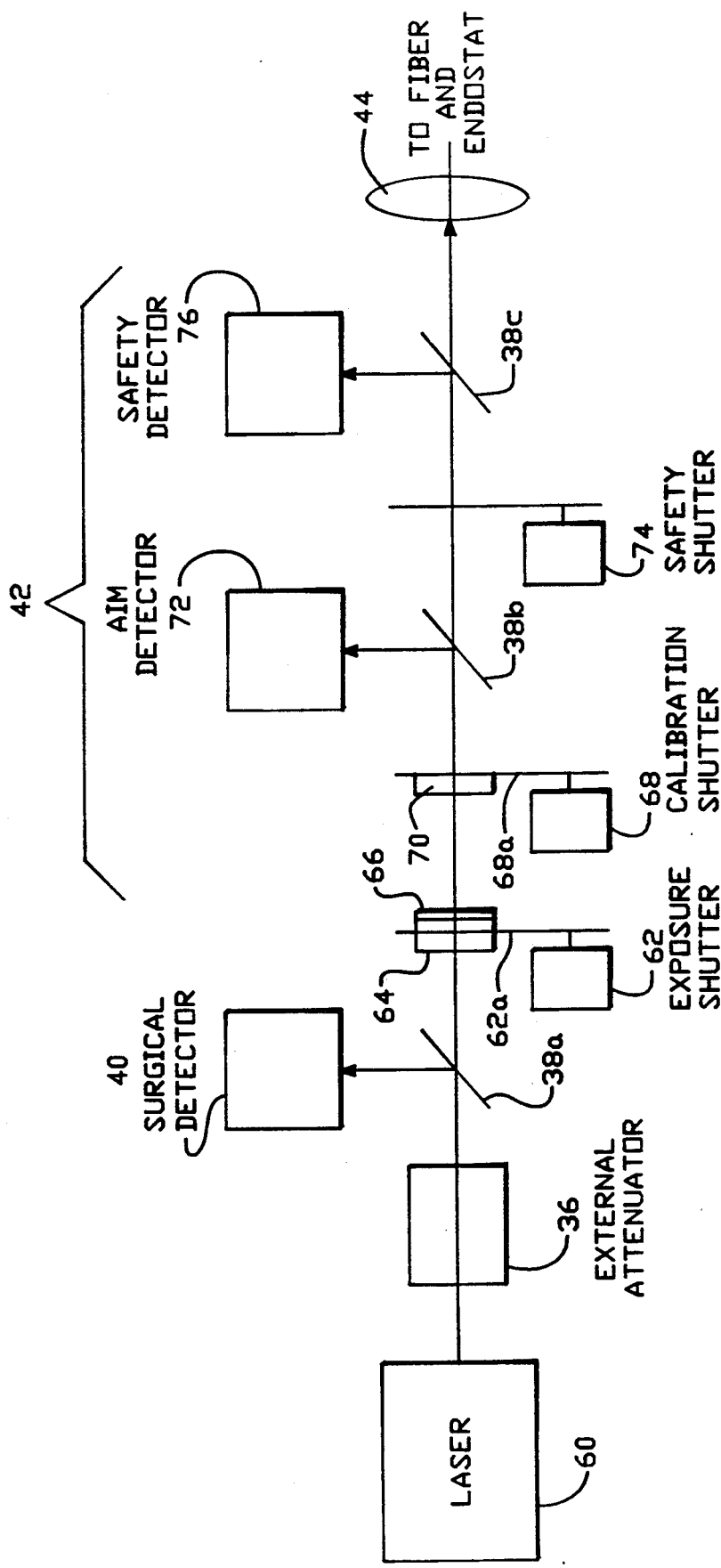
FIG. 5 is a block diagram of the optical filters, detectors, and other components in the beamline external to the laser.

FIG. 5 illustrates the beam path from the laser 60 to the fiber and endostat used by a surgeon or other operator of these laser systems. Mounted along the beam path are an external attenuator 36, which is composed of a half wave plate mounted on a stepper motor, and a pair of polarizers. As known in the art, by rotating the half wave plate, the amount of attenuation caused by the polarizers can be controlled. This allows a very large dynamic range of output power to be supplied. For instance, a 20 watt output beam from the laser 60 can be attenuated down to the milliwatt range.

Next along the path is a beam splitter 38a mounted to supply a sample of the beam to a surgical detector 40. This detector comprises in the preferred system a photodiode which generates an output voltage proportional to the intensity of light striking the photodiode. This output signal is then transmitted to the data processing system as illustrated in FIG. 1.

Next along the path is an exposure shutter 62. This exposure shutter 62 includes a 5 % transmission filter 64, and a light valve 66 on arm 62a. The light valve is implemented in the preferred embodiment with a liquid crystal assembly having a transmission at the output wavelength determined by a voltage supplied on its input. The control of the light valve is provided by the data processing system 34. Arm 62a can be moved into and out of the beam path under control of the data processor 34. This exposure shutter and light valve assembly is moved into place during the ready mode to allow precise control of the amplitude of the aim beam. The external attenuator 36 is not used in this mode because it is pre-calibrated for operation at the work output power mode as explained below.

After the exposure shutter 62 along the beam path is mounted a calibration shutter 68. The calibration shutter includes a 5% transmission filter 70 mounted on an arm 68a, which can be moved into and out of the beam path under control of the microprocessor.

The calibration shutter 68 is used to provide an even greater dynamic range in output power for both the high power work mode and the aim beam in the ready mode as is described in detail below.

Next along the optical path is a beam splitter 38b which supplies a sample of the beam to an aim detector 72. This detector can also be implemented using photodiode. The photodiode is coupled back to the data processor 34 which is used in controlling the output power during the aim mode.

After the aim detector 72, a safety shutter 74 is mounted on the beam path. This safety shutter can be moved in and out of the beam path to prevent an output from being supplied through the fiber for safety reasons. After the safety shutter 74, a third beam splitter 38c is included in the path which supplies a sample of the output beam to a safety detector 76. The safety detector 76 supplies a signal to the data processing system 34 which controls the safety shutter 74. Thus, when the beam at the safety detector 76 goes beyond a pre-specified value, then the microprocessor throws the safety shutter. This value, in a typical system, can be, for instance, 30% greater than a selected output power expected by a laser. Obviously, even greater precision can be provided if desired for particular applications.

Finally, along the beam path is a lens 44 through which the beam is coupled into a fiber and onto the endostat.

The external attenuator 36, exposure shutter 62, and calibration shutter 68 are used in combination with the pump power modes under control of the data processing system to provide a beam having desired output power to the fiber. This gives the data processing system, under program control, great flexibility in providing output power for a particular application.

Figure 6:
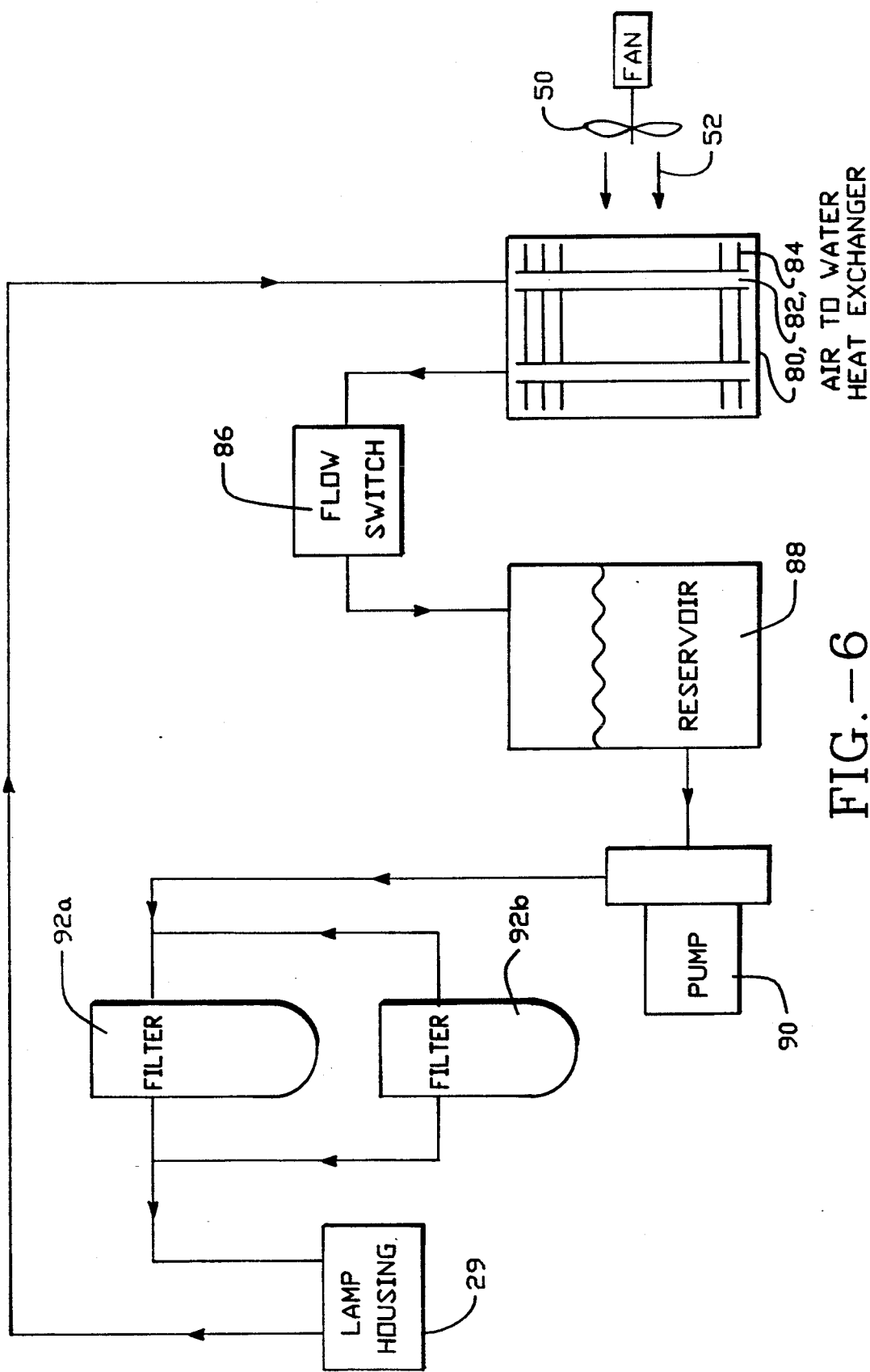
FIG. 6 is a schematic diagram of the internal water recycling system and the air-cooling system according to the present invention for the laser.

FIG. 6 illustrates the internal water recycling system and the air-cooling system. The fan 50 blows air 52 through the air to-water heat exchanger 80. The air-to-water heat exchanger 80 is of the tube 82 and fin 84 design. The waterflow is monitored with a flow switch 86. The pump 90 pumps water from the reservoir 88 through the filters 92a and 92b and the lamp housing 29. The filter 92a is a 0.5 micron particle filter and 92b is a deionizing filter.

The performance of the laser system depends on some important characteristics of the cooling system. The size of the heat exchanger and rate of airflow used will depend on the maximum temperature rise of the laser system for a given heat load. The size of the reservoir will depend on the initial rate of temperature increase when the laser goes to high power and other heat flow averaging effects desired for a given system. Those skilled in the art can readily design such a cooling system for a particular laser system. The rate that heat can be dissipated by the air cooling system is determinant of the average rate of waste heat produced by the laser system.

The air-cooling system effectively cools the laser according to the invention for extended periods of time depending on such parameters as the operating mode, power levels and the surrounding conditions (e.g., the operating room size and the cooling and ventilation systems of the operation room). In the work mode, more power is consumed and more heat is dissipated than in any other mode of laser operation. The air cooling system will effectively cool the laser in the work mode. However, if the laser is operated continuously in the work mode for extended time periods, the air cooling system may become less effective. As a result, laser output power will drop. The amount of any drop and the time at which the output power begins to drop will depend on the parameters set forth above. For example, in one embodiment, the output power dropped less than 25% within 30 minutes of operation in the work mode. After 30 minutes, the laser system stabilized.

FIGS. 7, 8, and 9 illustrate the output power versus pump power represented by input current to an arc lamp, curves for a Nd:YAG laser. FIG. 7 illustrates the output power characteristics for a cavity supplying the 1064 nm output without a Q-switch. The trace 700 illustrates the output power with a modulated pump current at approximately 80 Hz with a 50 % duty cycle. The trace 701 illustrates the output power versus average input current with a constant input current supplied. As can be seen, the modulated pump power results in higher gain in the cavity and greater output power for a given average input current even for systems without frequency doubling. It can be seen that the slopes of the modulated (trace 700) and unmodulated (trace 701) pump modes are about the same.

FIG. 8 illustrates the benefits of modulating the pump current in a frequency doubled system having a non-linear crystal and supplying the 532 nm output without a Q-switch. As can be seen at trace 800, in the constant pump mode, the output power folds back at about 27.5 amps of CW lamp current. This occurs because the thermal focusing of the YAG rod starts to cause large cavity losses at higher input currents. Thus, beyond the foldback point the output power actually decreases with increases in pump power. This characteristic foldback in frequency doubled system occurs typically between 26 and 30 amps of average lamp current. The trace 801 shows the effect of modulation. The slope of trace 801 is significantly higher than the slope of trace 800, illustrating the enhanced benefits of modulation for frequency doubled systems.

FIG. 9 illustrates the operation of a frequency doubled laser like that used to generate the curves of FIG. 8, with the addition of Q-switching. Q-switching increases the average output power for both the continuous pump power (trace 900) and modulated pump power (trace 901) modes. But, again, the slope of the trace 901 for the modulated pump power is significantly higher. Foldback of the second harmonic output power occurs at a higher value, for the particular laser tested at 31 amps. As can be seen, for the continuous pump power mode, in order to achieve 20 watts of output power, the laser must be operated near the foldback value. In the modulated pump power mode, the laser is operated well below the foldback point to achieve 20 watts of output power.

In the systems tested to generate the plot of FIG. 9, the highest average current in the modulated pump power mode is limited to 25 amps due to power supply limitations. In subsequent tests, with power supplies capable of supplying modulated pump power at an average in the 30 amp range illustrated the foldback phenomenon as well. However, the average output power at the second harmonic was much higher in the modulated case as is apparent from FIGS. 8 and 9.

Therefore, it can be seen that a modulated pump power mode contributes to superior performance of a frequency doubled laser system. For a given output power at the frequency doubled wavelength, a lower input pumping power is required. This results in less waste heat and consequently lower temperature operation of the system. At a lower temperature, there is less thermal focusing and higher gain in the Nd YAG rod. This allows the resonant cavity to stay within a range with low cavity losses due to thermal focusing and at a high power. Further, the response of the non-linear crystal to higher peak powers in the modulated mode results in more efficient conversion to the second harmonic power.

In the preferred system, the pump power modulation was operated at about 83 Hz with a 50% duty cycle. This value is chosen due to characteristics of the particular power supply, including the rise time, the hum generated by the switches required to implement the modulation and other factors. In general, modulation of the pump power supply is effective in the range of 0.5 Hz to as much as 200 Hz. In particular, the pump power modulation must be fast enough that the temperature of the gain medium does not fluctuate with each cycle of the pump power to a significant degree, but only responds to the average input power. This sets the lower limit of useful current modulation in a particular system.

The upper limit on modulation is set by the rise time of the pump power source and power supply. Also, the modulation in a preferred system should be much slower than any Q-switching so that it does not interfere with the Q-switching dynamics. Alternatively, the pumping should be coordinated with the Q-switching so that the objectives of the Q-switching are met.

Particular applications of the laser system may place other limits on the modulation frequency in the work mode. For instance, in the preferred application for surgical uses, modulation rates below 50 Hz or so, may have an effect on the continuity of any work being done on tissue. For instance, if the laser is used for cutting in vascular tissue, a rapid movement of an endostat delivering the beam might result in a row of holes in the tissue, rather than a continuous cut. It is found that a selected frequency above 50 Hz avoids this problem for surgical applications, with typical beam diameter and speed of cut.

As mentioned above, the ability to control the pump power mode of the laser using programmable data processors enables the laser system to be adapted to a variety of applications while optimizing the pump power modes. For instance, in the surgical application, it is desirable that the laser be air-cooled. However, it is necessary to generate an aim beam in one mode and to be able to transition very quickly from the aim beam to the work beam. The pump mode control allows operation of the laser to achieve these objectives. FIGS. 10a and 10b illustrate alternative pump modes for the preferred embodiment of the present system. As illustrated in FIG. 10a, for a surgical laser the pump power can be operated in three modes in combination with a Q-switch. In the first mode, labelled standby 1000, a low lamp current is generated in the range of approximately 6 amps for the krypton lamp described above. In this mode, the lamp is receiving sufficient current to be on. However, there is not enough pump power being delivered to the gain medium to push the laser resonator over threshold so that output power is generated. In the second mode 1001, labelled the ready (aim) mode, the lamp current is increased to an intermediate level. At this intermediate level, sufficient lamp current or pump power is supplied to thermally stabilize the resonator above laser threshold. As illustrated in FIG. 10a, a continuous pump mode can be used to achieve this goal. To do this, the lamp current/pump power must be high enough that the laser is thermally stable, but allows quick transition to the high power work mode. For the embodiment illustrated in FIG. 1, it is found that this average current is about 20 amps. The output power generated with a non-Q-switch CW pump mode is relatively low at the second harmonic frequency. Thus, in this continuous pump mode, it may be necessary to provide an external source for providing an aim beam as discussed above.

However, the laser resonator is maintained in a condition which allows rapid transition from the ready mode 1001 to the high power work mode 1002. In this case, the data processor is able to set the operating pump power at a level to achieve a desired output power up to the foldback level. In FIG. 10a, the dotted line 1003 illustrates that the operating current, to achieve a given output power in the high power mode may vary with time. Using the data processor to control the pump power in the various modes allows use of a servo lop to maintain the output power at a desired level.

As can be seen, the Q-switch is not used in either the standby mode 1000, or the low power ready mode 1001. It is turned on for the high power mode 1002 in order to take advantage of the effective high peak powers on the extraction of the frequency doubled output from the non-linear crystal.

FIG. 10b illustrates an alternative programmable pump power scenario according to the present invention. As illustrated in FIG. 10b, the standby mode 1000 operates in the same manner as the standby mode 1000 illustrated in FIG. 10a. On the other hand, in the ready mode 1001, a modulated pump power is supplied as illustrated at line 1004. This modulated pump power allows greater frequency doubled output at 532 nm for a given average pump power as described above with reference to FIG. 8. No Q-switching is used in this mode. However, the average pump power is maintained at about the same level as is required to keep the resonator thermally stable and allow a quick transition to the high power work mode 1002. This high power work mode 1002 in the embodiment of FIG. 10b is operated in the same manner as described above with reference to FIG. 10a.

As mentioned above, the transition from the ready mode to the high power mode in which work is to be accomplished with the beam, can be a critical feature of many laser systems, such as surgical systems. For instance, in a surgical system, this transition must occur with no perceptible delay to the surgeon, and without a large overshoot, which might trip safety features on the surgical laser system.

Figure 11:
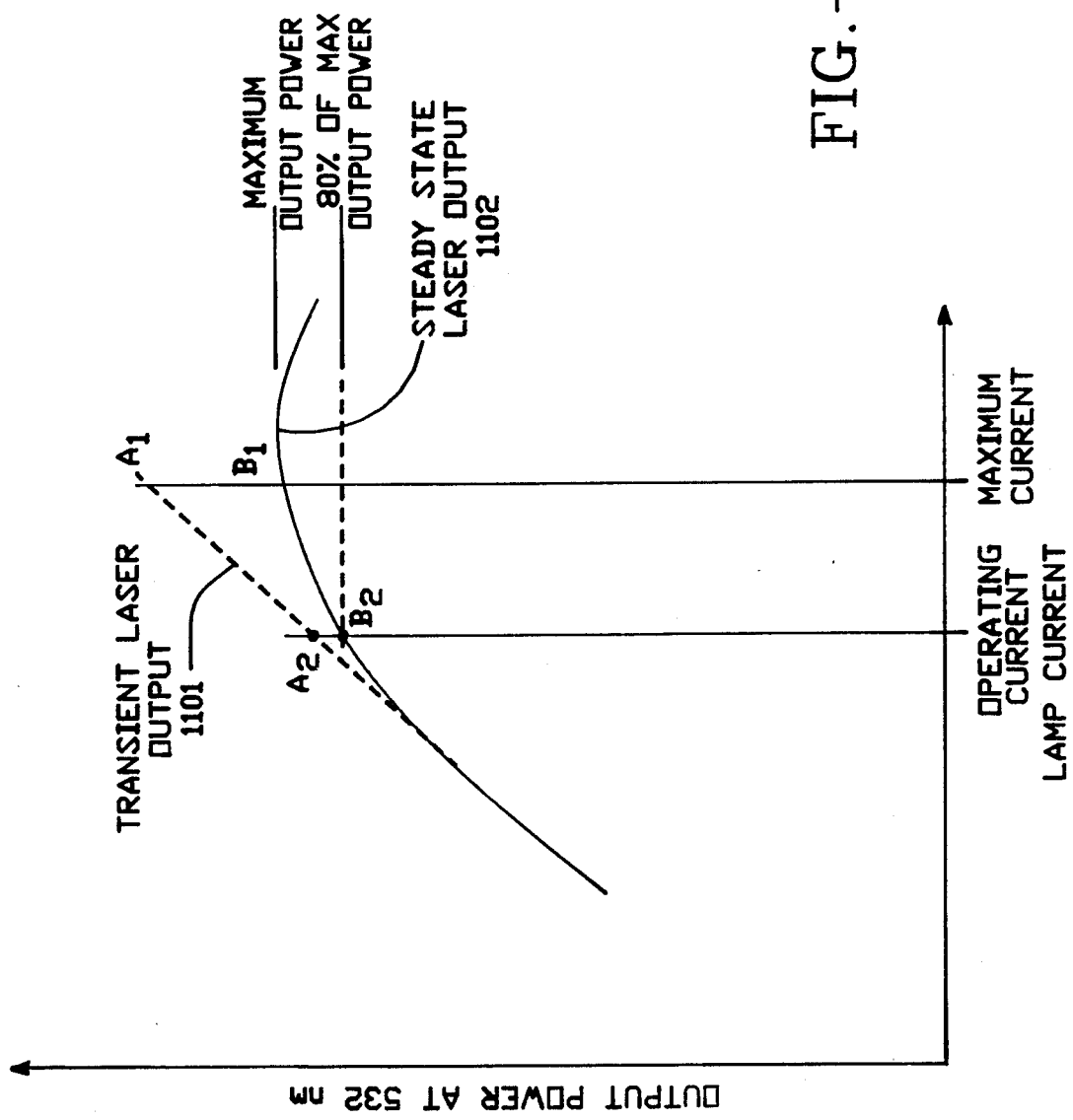
FIG. 11 shows a typical curve of the laser output power at 532 nm versus lamp current as recorded during warmup and illustrates the dynamics of the laser during the transition from the ready mode to the work mode.

Overshoot is explained with reference to the plot in FIG. 11. During the transition from the ready mode to the work mode, the pump power is rapidly increased. As this power increases, the gain in output power of the laser follows the pump power relatively closely. However, the temperature change of the gain medium will fall behind this increase in pump power slightly. Therefore, because the gain of the laser is higher at lower temperatures of the solid state gain medium, and because thermal focusing and other distortions lag, the output beam will tend to follow the transient laser output trace 1101 during the transition. As the temperature of the gain medium increases, the power will then fall back to the steady state laser output trace 1102. As can be seen, as the pump power rapidly transitions to a maximum pump power, the output power of the laser at the 532 nm line can be significantly above the expected maximum output power of the laser. This can cause safety features on surgical laser systems and the like to be tripped resulting in premature shutdowns and other troublesome operational hassles.

For instance, if the pumping mode transitioned directly to the maximum current, the output power would rise quickly to the level A1 in the figure, and then slowly decay to the level B1 as the resonator became thermally stabilized. However, according to the present invention, during the transition, the pump power is controlled so that the current supplied to the lamp in this embodiment is moved rapidly to the point where output power reaches the level A2 or approximately 80% of the maximum output power desired for the high power mode. At this point, the potential overshoot from the point A2 to the point B2 is much smaller and acceptable. At this point, a closed loop servo relying on the surgical detector and the desired maximum output power for the particular application, is utilized to control the pump power, by controlling the lamp current in the embodiment described.

The data processing system provides significant capability for the laser system to optimize the pump power and output power of the laser system for particular applications. In the preferred system, as mentioned above, is a Nd:YAG solid state laser with a KTP crystal used in generating a 532 nm green output beam, used for surgical applications. In this system, the data processor is programmed to operate in a warm-up mode when the system is first turned on during which the laser system is exercised to measure parameters of the laser system used to generate the output beam in various modes. These measured parameters provide a characterization of the laser system over a range of operating conditions that is stored for use in controlling the laser system as described below. Also, after the warm-up mode, the laser system can enter a standby mode during which the pump power source, the lamp in this case, is maintained on with a small current but below laser threshold so that no output beam is produced. During the standby mode, the processor can also exercise the system in response to user inputs to adjust the output power for a low power mode such as used in aiming the beam, and to adjust the output power for a high power mode,, such as used for accomplishing work with the beam.

Further, the data processing system can operate the laser system during a low power mode based on parameters generated during the characterization in the warm up and aim adjust modes, using a servo control loop to maintain the output power at the desired level by adjusting the light valve or the pump power. Finally, in the high power mode in which work is accomplished, the data processor uses the stored characterization developed during the warm-up or power adjust modes to establish a pump power mode and settings for the surgical attenuator and calibration shutter. Again, the desired output power is maintained using a servo control loop in which the surgical attenuator and pump power are adjusted dynamically to maintain a constant output power.

Also, the data processing system is utilized to perform a variety of other tests during the warm-up, or other modes of operation of the laser system, designed to test specific components in the beam path and to provide certain safety checks. These other processes are not relevant to the present invention and will not be further discussed.

In the preferred system, the characterization during the warm-up mode is performed for both the low power ready mode and the high power work mode, independently. This occurs because the low power mode uses a modulated pump source, while the high power output mode uses a continuous pump source.

Figure 15:
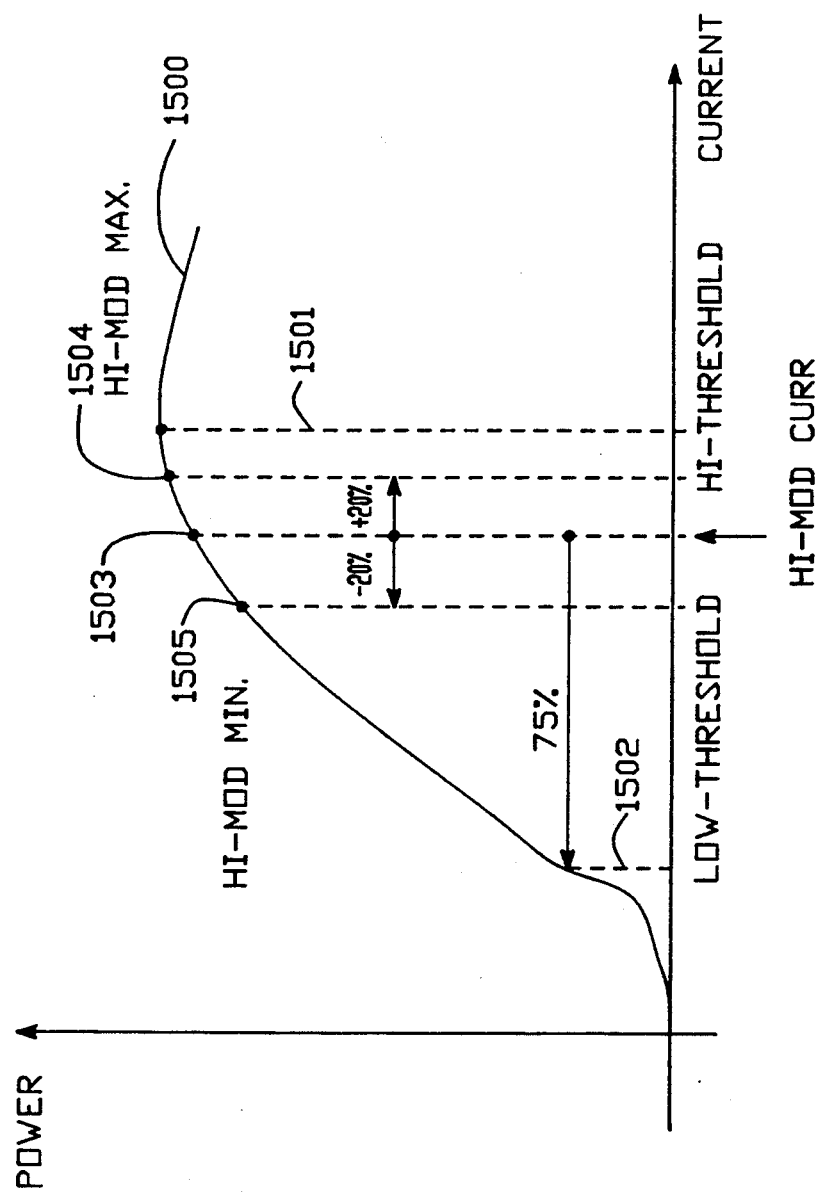
FIG. 15 shows a plot of power versus peak pump power during modulation, used for describing calibration for the ready mode according to the present invention.

For the aim mode, during warm-up, an output power versus input current to the lamp parameter curve is built up. This is carried out by setting the peak modulation current at 20 amps on channel B of FIG. 4. The low modulation current is held constant at 5 amps. The laser is run for second then the average output power at the surgical detector is determined over 0.5 seconds. The value is then stored and the peak modulation current is increased by one amp. This process continues until a peak modulation current of 40 amps has been exercised resulting in a set of data defining a plot like trace 1500 in FIG. 15. The data processor then uses the parameters measured to determine a low threshold point 1502 and high threshold point 150 for the modulated pump mode. The low threshold 1502 is defined as the peak current where the system starts lasing, or where at least three watts of output power is generated. The high threshold 1501 is defined as the peak current at which the power starts to decrease with an increase in current; where the output power is greater than 21 watts; or where the current through the lamp is greater than 38 amps. Based on these low and high threshold currents, a peak modulation current for the aim beam, and minimum and maximum currents allowed during aim power adjustment in the ready mode are set. The nominal value HI_MOD_CURR for the peak modulation current during the ready mode is set according to the following equation:

$$HI\_MOD\_CURR = 0.75(HI\_THRESHOLD - LO\_THRESHOLD) + LO\_THRESHOLD$$

Next, a maximum peak current HI_MOD_MAX is determined according to the following equation:

$$HI\_MOD\_MAX = HI\_MOD\_CURR + 0.2(HI\_THRESHOLD - LO\_THRESHOLD)$$

Finally, a minimum current HI_MOD_MIN for the peak modulation value is set according to the following equation:

$$HI\_MOD\_MIN = HI\_MOD\_CURR - 0.2(HI\_THRESHOLD - LO\_THRESHOLD)$$

As can be seen, the nominal peak current is defined at point 1503 on the graph as a value that is above the low threshold by 75% of the difference between the low threshold and the high threshold. The maximum peak modulation current is defined at point 1504 which is equal to a value that is 20% greater than the nominal value at point 1503. Similarly, the minimum peak modulation current is defined at point 1505 which is 20% below the nominal value at point 1503.

The aim beam in the present system has a low, medium, and high setting. In the low setting, approximately 0.2-0.3 milliwatts is generated at the output. In the medium setting, approximately 1 milliwatt is generated and in the high setting, approximately 4 milliwatts is generated. During the calibration mode, set points on the light valve and the point at which the calibration shutter is moved into place to accomplish various aim levels are determined. This is determined by placing the exposure shutter 62 in the beam path and setting the light valve with a threshold voltage plus 2 volts RMS. This causes certain attenuation of the beam going through the exposure shutter. Therefore, the light valve is never completely clear during the aim mode. Thus, the calibration shutter drops with higher pump power to achieve the lower aim modes as required. The software determines the optimum setting of the calibration shutter and the light valve to achieve the three modes and stores these set points.

During the ready mode in which the aim beam is being delivered through the fiber, the light valve is used to maintain the aim beam at the desired power level in combination with adjustments of the pump power. The algorithm involves using the pump power from the optimum point HI_MOD_CURR to increase the output power up until the maximum peak power HI_MOD_MAX is reached. When that maximum is reached, the light valve voltage is decreased to reduce dispersion at the light valve and therefore increase the aim beam power. At the opposite extreme, when the minimum peak modulation current HI_MOD_MIN is reached when trying to reduce the aim power, then the light valve voltage is increased to increase the dispersion and decrease the output aim beam.

Also during characterization generated during the warm-up mode, maximum and minimum pump powers for the work mode are determined. This is accomplished by first warming up the lamp with pump power. Then the Q-switch is turned on. Then an output power versus input current to the lamp curve is generated and stored for the green power mode. This is accomplished by setting the current to a constant 25 amps through the channel C in FIG. 4. Then the power at the surgical detector is measured. Next, the current is increased in steps of 600 milliamps and power is measured after 2 seconds. This step is repeated until the power level reading levels off, the power reading decreases for two consecutive milliamp increments, the current reaches 40 amps, or the power achieved is greater than 27 watts. This process is carried out with the surgical attenuator fully open.

During the standby or ready modes, a power adjust mode can be entered when a user sets a desired output power for the particular application This adjust mode utilizes the curve generated during the characterization performed during warm-up to set the lamp current and the surgical attenuator and calibration shutter settings to achieve the desired power. In this mode, the output of the DAC on channel C in FIG. 4 is set to the value that is equal to about 80% of the peak power detected during the characterization mode for the work mode. After an initial warm-up, the system takes the time it needs to adjust to the requested power by lowering the pump current and/or adjusting the shutter and filters in the beam path. When the surgical attenuator is set during this work power adjust mode, it is left at the determined value because it is a relatively slow moving filter. Therefore, the ready mode aim beam set points must be readjusted to account for any changes in the surgical attenuator that are made. This can be accomplished by returning to an aim adjust mode and no new characterization of the system is necessary.

As mentioned above, the data processor also operates the laser during the transition from the aim mode to the work mode to avoid overshoot, as explained with reference to FIG. 11.

In particular, during the transition which must occur within less than 200 milliseconds, the system changes to a power adjust mode and sets the current to the nominal current value with low RF. Next, the current is set to the nominal current and waits 80 milliseconds to warm up the laser. Then both the calibration shutter and the exposure shutter are raised. Then, the current is set to a value 20% lower than the nominal current determined during the power adjust mode for 2 milliseconds. Then the Q-switch is turned on at high RF for one millisecond. The current is then set to a value 5% lower than the nominal current. If a continuous exposure is being carried out, the software measures the output at the surgical detector every 5 milliseconds. The software then controls the pump power to adjust the power back to 100% of the desired output power.

Attached as an Appendix to the present application are routines written in the C programming language to provide details concerning implementation of the preferred system for those skilled in the art. These include routines for performing the calibration algorithms, the adjustment algorithms, the control loops for maintaining the output power, and the algorithm for preventing overshoot of the beam during transition from the ready to work modes.

As can be seen, the capability of the present invention to change pump power modes and control beamline components using a data processing system provides significant flexibility in the design of frequency doubled laser resonators. Many of the shortcomings of conventional lasers are therefor overcome. For instance, the closed loop servos for maintaining output power allow continuous adjustment of lamp current to compensate for changes in the gain medium and other components, as temperature changes. Also, the characterization routine during warmup allows compensation for aging of pump sources, such as arc lamps. As arc lamps age, the operating current must be higher to achieve a given pump power. When the operating current of a lamp reaches an upper limit determined by a lamp manufacturer, the lamp has reached the end of its useful life and a message can be generated by the data processor that a lamp change is required. Also, the characterization routines run by the data processing system automatically compensate for changes in current required due to lamp aging.

As mentioned above, these characterization routines are implemented at power up, each time the laser system is turned on, and alternatively in response to other user inputs so that the laser system may be re-characterized from time to time to account for changing characteristics of elements of the laser system over tie. Furthermore, this re-characterization is carried out automatically without output from a factory representative or other trained operator. In one embodiment of the present invention, a sensor (e.g., sensor 57, FIG. 1) is mounted with the laser system and coupled to the data processor 34. The sensor is designed to indicate changes in environmental conditions which may affect the operation of the laser system. In the event that the temperature changes significantly in the operating room or some other key environmental condition changes, the sensor would direct the microprocessor to perform a characterization of the laser system and adjust the operating parameters accordingly.

In addition, the characterizations of the laser system that are carried out from time to time are stored in memory of the data processor 34 to provide a characterization log. Either all of the characterizations can be stored in a log, or a specialized history in a compressed form can be created. The characterizations of the laser system provide a tremendous amount of information useful in diagnosing problems with the laser system, and understanding the operation of these complex systems over time. The modem 56 can then be used for accessing this log of characterizations of the system from a remote station by a trained operator. The information can then be analyzed and a program for carrying out corrective action can be sent back to the processor 34 through the modem 56 to adapt to any perceived change in operation of the system.

The modem can also be used for sending software upgrades to the processor, or new routines that can be used for carrying out new applications of the system.

Figure 12:
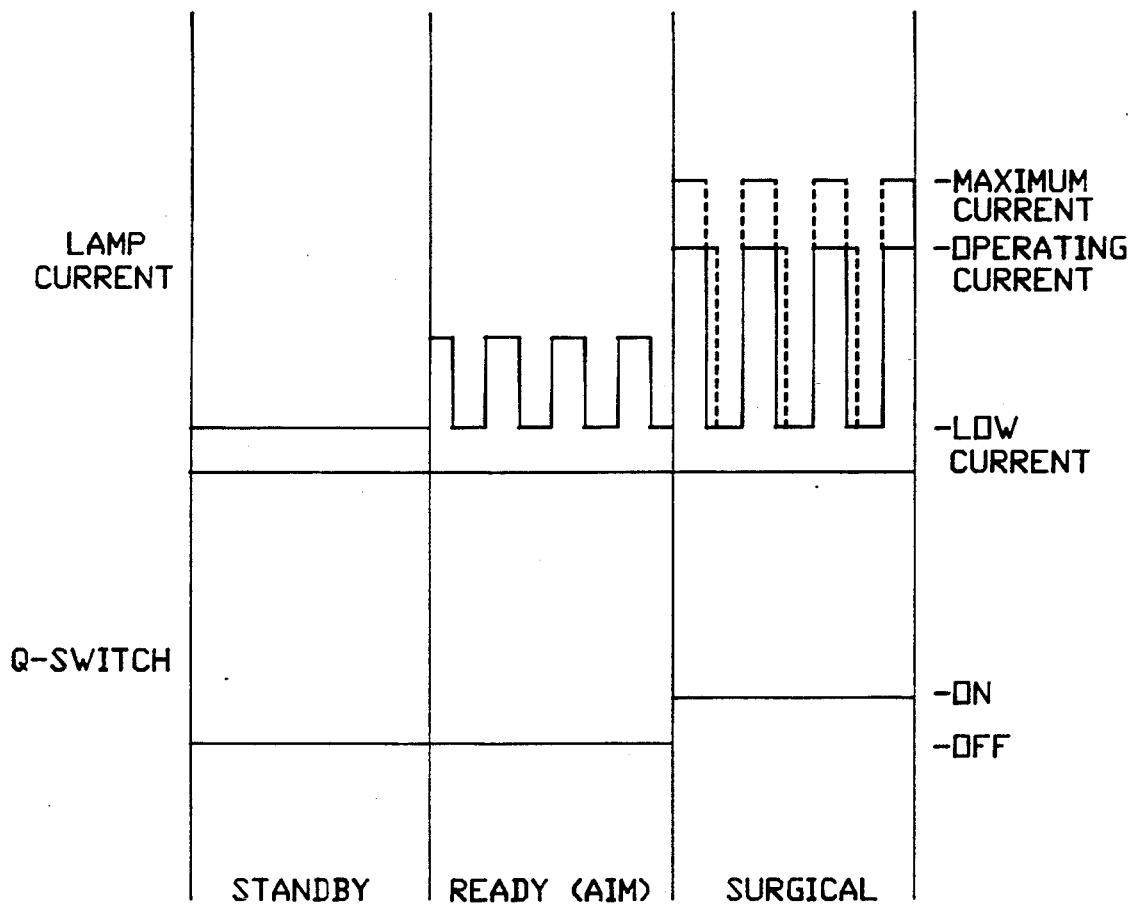
FIG. 12 shows the lamp current waveforms and Q-switch control signals during the standby, ready, and work modes of another embodiment of the invention where the lamp current is modulated during the work mode.

As mentioned above, in a preferred embodiment of the present invention, the pump source is not modulated during the work mode and a Q-switch is utilized to achieve the high peak powers desirable for second harmonic generation. According to an alternative embodiment, the laser may be operated in the work mode with a modulated pump source in combination with a Q-switch, as illustrated in FIG. 12. According to the embodiment illustrated in FIG. 12, the standby and ready modes are operated in the same manner as illustrated with respect to FIG. 10b. However, in the work mode, the lamp current is modulated. The data processing system has the capability to select a desirable peak modulation current and a desirable duty cycle as suits the need of a particular application. Further, with modulation in both the ready and work modes, greater frequency doubled output for a given average pump energy can be achieved. In principle, the duty cycle of the pump modulation can vary over a wide range, for instance, from less than 1% to greater than 99%. At higher duty cycles and shorter pulse widths for the pump source, the dynamics of the Q-switching may be affected and the characteristics of the Q-switch must be taken into account.

The embodiment illustrated in FIG. 12, where the Q-switch and pump modulation is used in the work mode, may be desirable to improve conversion efficiency for second harmonic generation in weaker lines of the solid state lasers, for example, for doubling the 1318 nm line in Nd:YAG to generate the 659 nm output. There are a large number of lines available in such solid state mediums. Such are listed in Koechner, *Solid-State Laser Engineering*, Springer-Verlag, 1988, 2d Edition, p. 53, which is incorporated by reference to illustrate other lines with weaker gain to which the present invention may be particularly suited. By proper programming of the data processing system, the pump modes may be optimized for each particular line, and the laser resonator may be adapted as necessary. For instance, one laser resonator adapted for generation of the 659 nm line is illustrated in co-pending U.S. patent application entitled Medical Laser Apparatus, High Powered Red Laser Used In Same, and Laser Resonator with Non-Linear Output, filed on Dec. 18, 1990, Ser. No. 07/631,697, which was owned at the time of invention and is currently owned by the same Assignee as the present invention. Achievement of frequency doubling with these weaker gain lines is enhanced because the modulation of the pump source allows driving the resonator higher above laser threshold during the peak of the cycle to achieve efficient output power, and the Q-switch improves conversion efficiency to the second harmonic.

Figure 13:
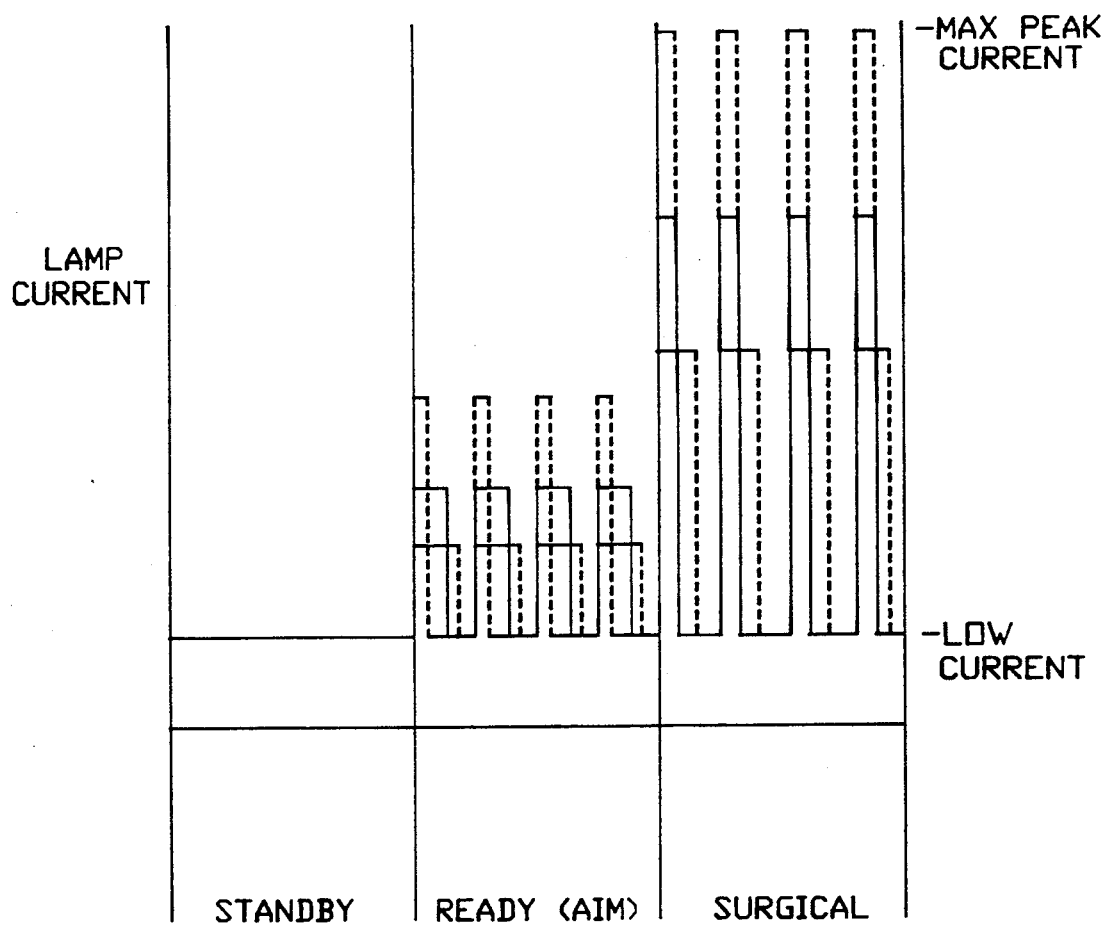
FIG. 13 shows the lamp current waveforms during the standby, ready (aim), and work modes of yet another embodiment of the invention where the lamp current is strongly modulated or pulsed during the work mode.

In an alternative embodiment, the Q-switch may be eliminated. According to this third embodiment, as illustrated in FIG. 13, the pump power source is modulated in both the ready and work modes. However, Q-switching is not necessary in the work mode. It is found that to attain an enhancement in power of second harmonic generation by a factor of 6, the pump power source must be modulated so that the peak fundamental power increases by a factor of 6. This can be achieved in the laser system illustrated in FIG. 1 with a peak power of about 19 kW using the krypton arc lamp from FIG. 3b, at currents of about 105 amps and 170 volts. This is well within the specifications of the krypton arc lamp.

In order to demonstrate that pump power modulation achieves substantial enhancement in second harmonic generation such that Q-switches would not be necessary for practical systems, three power supplies were operated in parallel providing the capability to generate peak current pulses of up to 200 amps. An average second harmonic power in the range of 15–20 watts was attained with pulse widths of 1–6 milliseconds and repetition rates of 20–200 Hz. Further enhancements could be achieved by adjustments in the cavity parameter, such as spotsize ratio of the Nd:YAG rod and the KTP crystal. It is expected that by increasing this spotsize ratio over that described above, by as much as 30%, improvements in output power could be obtained.

Figure 14:
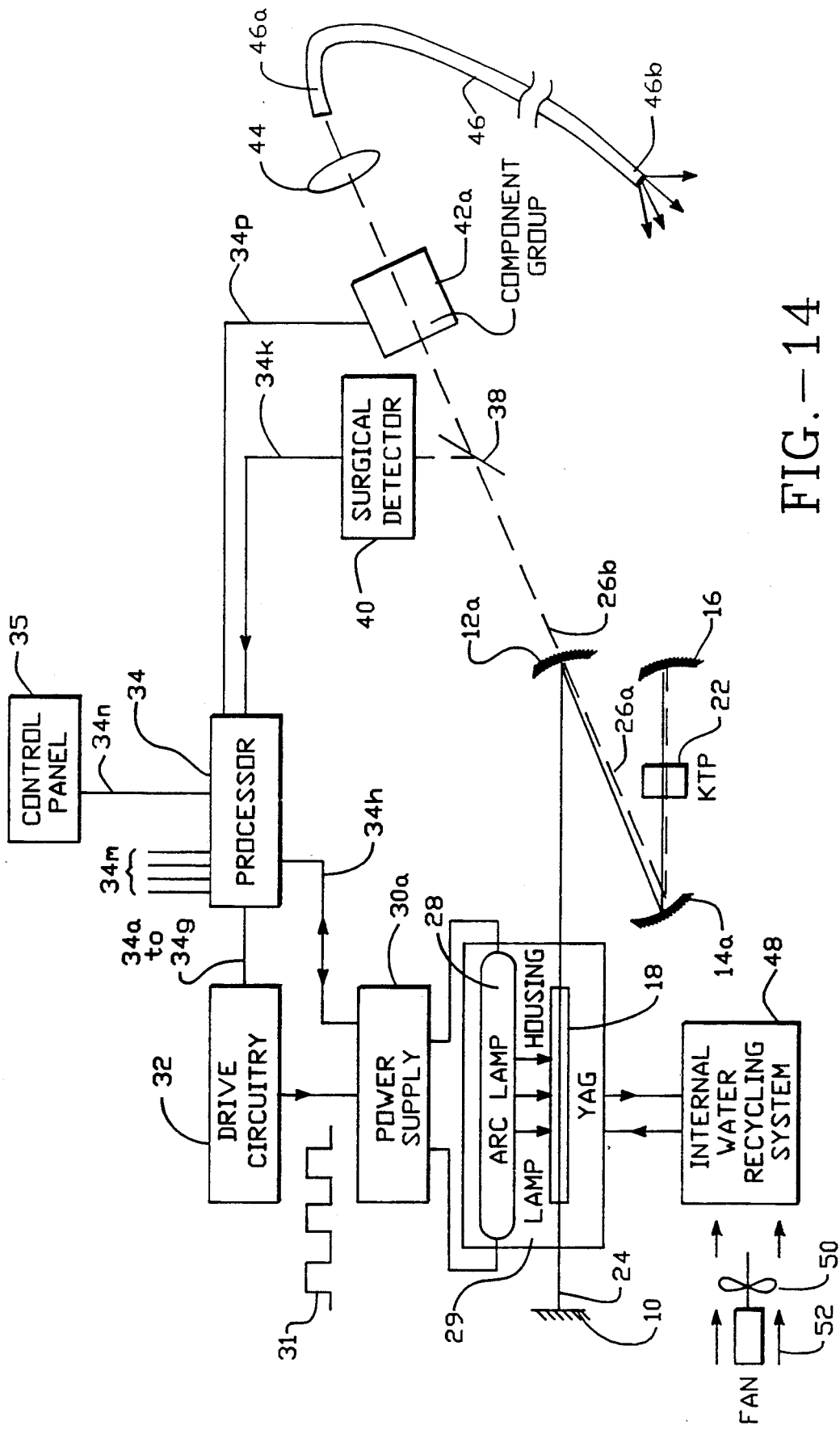
FIG. 14 shows a block diagram of the laser system for an alternative embodiment of this invention.

As illustrated in FIG. 14, the laser system can be modified by removing both the Q-switch and the external surgical attenuator. The hardware components of the system of FIG. 14 are the same as in FIG. 1, and like reference numbers are used. The components are not recited here. The Q-switch and surgical attenuator are removed because the modulated pump power provides a great deal of flexibility in controlling the output power of the laser not attainable using a Q-switch. The data processing system can be programmed to maintain a constant thermal load in the laser system while varying the peak pump power widely. Thus, the peak current and duty cycle of the pump power source can be adjusted in such a way to keep the average pump power constant, but the second harmonic power during the ready and work modes adjusted by selecting the peak current and duty cycle. Although it may be necessary to use attenuators in the beamline during the ready mode in order to extract an aim beam, such attenuators may well be eliminated for the work mode. The average power does not have to be constant, rather it can be maintained at levels which keep thermal focusing of the gain medium within the range of stability of the resonator. In a preferred system, the input current of the lamp source has been demonstrated using currents modulated from 5 amps minimum to 140 amps peak at 83 Hz with pulse widths as small as 2 milliseconds. The ratio of the spotsize in the rod and the non-linear crystal range from 2.5 to 4.0.

Thus, according to the embodiment of the present invention illustrated in FIG. 14, a less expensive laser system could be achieved without a Q-switch and with greater control over the output beam of the resonator. This leads to less expensive and simpler systems for laser surgery and makes such systems available in more places.

The preferred system is adapted particularly to laser surgery by a generation of the second harmonic of the 1064 nm line from a Nd:YAG laser using a non-linear crystal comprised of KTP The system can be air-cooled, has low power consumption, making it a desirable system for providing laser surgery in a large number of places.

The present invention can also be applied to a much larger class of applications, including photodynamic therapy, dermatology, and other medical uses. Also, the laser can be used in industrial applications which may have a need for beams extracted from a laser resonator using non-linear crystals for frequency doubling, or which may benefit from the laser system characterization techniques of the present invention.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical application, thereby enabling others skilled in the art to understand the invention for various embodiments and with various modifications as are suited to the particular use contemplated. It is intended that the scope of the invention be defined by the following claims and their equivalents.

What is claimed is:

1. A laser system comprising:
   a laser resonator for resonating at a first frequency;
   a gain medium, mounted within the laser resonator;
   controllable means, coupled with the gain medium, for supplying pump power in response to at least one control signal, to the gain medium to induce laser gain;
   means, mounted with the laser resonator, for extracting an output beam at a second frequency derived from the resonating first frequency, the output beam having an output power; and
   control means, connected to the controllable means, for supplying the at least one control signal to control the output power, wherein the control means supplies the at least one control signal in a first mode to generate a low output power, in a second mode to generate a high output power.

2. The laser system of claim 1, further including:
   input means, coupled to the control means and operated by a user, for selecting the first mode and the second mode; and
   wherein the control means supplies the at least one control signal in response to the input means to effect a transition from the first mode to the second mode without uncomfortable delay relative to the user's reaction time.

3. The laser system of claim 1, wherein the controllable means includes:
   means, responsive to the at least one control signal, for generating an electrical power signal having characteristics specified by the at least one control signal;
   means, connected to receive the electrical power signal, for transducing the electrical power signal to generate the pump power according to the characteristics of the electrical power signal; and
   the control means supplies the at least one control signal in at least the first mode to generate modulated pump power with a selectable low pump power and a selectable peak pump power.

4. The laser system of claim 3, wherein the controllable mean comprises an arc lamp.

5. The laser system of claim 1, wherein the control means supplies the at least one control signal during the first mode to modulate the pump power.

6. The laser system of claim 5, wherein the control means supplies the at least one control signal in the second mode to supply unmodulated pump power.

7. The laser system of claim 5, wherein the control means supplies the at least one control signal in the second mode to supply modulated pump power.

8. The laser system of claim 1, further including:
   means, mounted in the laser resonator and responsive to the control means, for Q-switching the laser resonator.

9. The laser system of claim 1, wherein the second frequency is a second harmonic of the first frequency.

10. The laser system of claim 1, further including:
    means, coupled with the laser resonator and the gain medium, for dissipating waste heat in air surrounding the system.

11. The laser system of claim 1, wherein the means for extracting comprises a non-linear optical crystal and an output coupler inside the laser resonator for transmitting at the second frequency.

12. The laser system of claim 1, wherein the means for extracting comprises a non-linear optical crystal outside the laser resonator.

13. The laser system of claim 1, wherein the gain medium comprises a solid state medium characterized by thermal lensing.

14. The laser system of claim 1, wherein the control means further supplies the at least one control signal in a transition from the first mode to the second mode so that the output power does not overshoot the high output power during the transition by more than a determinant maximum amount of overshoot.

15. The laser system of claim 1, further including:
    means, coupled with the laser resonator, for delivering the output beam to a workpiece; and
    means, coupled with the control means, for supplying user input;
    wherein the control means is responsive to the user input to operate in the first mode at the low output power for aiming the output beam on the workpiece, and in the second mode at the high output power for accomplishing work on the workpiece.

16. The laser system of claim 1, wherein the control means comprises data processing means, operable under program control, for generating the at least one control signal.

17. The laser system of claim 15, further including:
    means, mounted with the means for extracting and the data processing means, for supplying measurements of the output power to the data processing means; and input means, connected to the data processing means, for supplying user inputs setting a desired low output power and a desired high output power; and wherein the data processing means supplies the at least one control signal in a characterization mode to determine laser parameters based on pump power versus output power measurements for the first mode and for the second mode, and is responsive to the laser parameters, the desired low output power and the desired high output power to generate the low output power and high output power in the first mode and the second mode, respectively.

18. A laser system comprising:

a laser resonator for resonating at a first frequency;

a gain medium, mounted within the laser resonator;

controllable means, coupled with the gain medium, for supplying pump power in response to at least one control signal, to the gain medium to induce laser gain;

means, mounted with the laser resonator, for extracting an output beam at a second frequency derived from the resonating first frequency, the output beam having an output power;

means, coupled with the gain medium, for dissipating a determinant amount of waste heat in air surrounding the laser system; and control means, connected to the controllable means, for supplying the at least one control signal to control the output power, wherein the control means supplies the at least one control signal in a first mode to generate a low output power with modulated pump power, and in a second mode to generate a high output power, so that an average pump power remains low enough during normal operation of the laser system that waste heat generated by the laser system remains less than the determinant amount of waste heat.

19. The laser system of claim 18, further including:

input means, coupled to the control means and operated by a user, for selecting the first mode and the second mode; and wherein the control means supplies the at least one control signal in response to the input means to effect a transition from the first mode to the second mode without uncomfortable delay relative to the user's reaction time.

20. The laser system of claim 18, wherein the control means supplies the at least one control signal in the second mode to supply unmodulated pump power.

21. The laser system of claim 18, wherein the control means supplies the at least one control signal in the second mode to supply modulated pump power.

22. The laser system of claim 18, wherein the controllable means includes:

means, responsive to the at least one control signal, for generating an electrical power signal having characteristics specified by the at least one control signal;

means, connected to receive the electrical power signal, for transducing the electrical power signal to generate the pump power according to the characteristics of the electrical power signal; and the control means supplies the at least one control signal in at least the first mode to generate modulated pump power with a selectable low pump power and a selectable peak pump power.

23. The laser system of claim 22, wherein the controllable means comprises an arc lamp.

24. The laser system of claim 18, further including:

means, mounted in the laser resonator and responsive to the control means, for Q-switching the laser resonator.

25. The laser system of claim 18, wherein the second frequency is a second harmonic of the first frequency.

26. The laser system of claim 18, wherein the means for extracting comprises a non-linear optical crystal and an output coupler in the laser resonator for transmitting at the second frequency.

27. The laser system of claim 18, wherein the means for extracting comprises a non-linear optical crystal outside the laser resonator.

28. The laser system of claim 18, wherein the gain medium comprises solid state medium characterized by thermal lensing.

29. The laser system of claim 18, further including:

means, coupled with the laser resonator, for delivering the output beam to a workpiece; and means, coupled with the control means, for supplying user input;

wherein the control means is responsive to the user input to operate in the first mode at the low output power for aiming the output beam on the workpiece, and in the second mode at the high output power for accomplishing work on the workpiece.

30. The laser system of claim 18, wherein the control means comprises data processing means, operable under program control, for generating the at least one control signal.

31. The laser system of claim 30, further including:

means, mounted with the means for extracting and the data processing means, for supplying measurements of the output power to the data processing means; and input means, connected to the data processing means, for supplying user input setting a desired low output power and a desired high output power; and wherein the data processing means supplies the at least one control signal in a characterization mode to determine laser parameters based on pump power versus output power measurements for the first mode and for the second mode, and is responsive to the laser parameters, the desired low output power and the desired high output power to generate the low output power and high output power in the first mode and the second mode, respectively.

32. A surgical laser system comprising:

a laser resonator for resonating at a first frequency;

a solid state gain medium, mounted within the laser resonator, characterized by thermal lensing;

controllable means, coupled with the gain medium, for supplying pump power in response to at least one control signal, to the gain medium to induce laser gain;

means, including a non-linear optical crystal mounted with the laser resonator, for extracting an output beam at a second frequency derived from the resonating first frequency, the output beam having an output power;

means, coupled with the gain medium, for dissipating a determinant amount of waste heat in air surrounding the laser system;

means, coupled with the laser resonator, for delivering the output beam to a work site;

input means for supplying user input; and data processing means, responsive to a program and the user input and connected to the controllable means, for supplying the at least one control signal to control the output power, wherein the data processing means supplies the at least one control signal in a first mode to generate a low output power with modulated pump power used for aiming the output beam on the work site, in a second mode to generate a high output power for accomplishing work on the work site, and so that an average pump power remains low enough during normal operation of the laser system that waste heat generated by the laser system remains less than the determinant amount of waste heat.

33. The laser system of claim 32, wherein the controllable means includes:
means, responsive to the at least one control signal, for generating an electrical power signal having characteristics specified by the at least one control signal;
means, connected to receive the electrical power signal, for transducing the electrical power signal to generate the pump power according to the characteristics of the electrical power signal; and
the data processing means supplies the at least one control signal in at least the first mode to generate modulated pump power with a selectable low pump power and a selectable peak pump power.

34. The laser system of claim 33, wherein the controllable means comprises an arc lamp.

35. The laser system of claim 32, further including:
means, mounted in the laser resonator and responsive to the data processing means, for Q-switching the laser resonator at least during the second mode.

36. The laser system of claim 32, wherein the second frequency is a second harmonic of the first frequency.

37. The laser system of claim 32, wherein the means for extracting comprises a non-linear optical crystal and an output coupler inside the laser resonator for transmitting at the second frequency.

38. The laser system of claim 32, wherein the means for extracting comprises a non-linear optical crystal outside the laser resonator.

39. The surgical laser system of claim 32, wherein the data processing means further supplies the at least one control signal in a third mode for keeping the controllable means supplying pump power at a low level without generating an output beam wherein average pump power remains low enough during normal operation in the first, second and third modes of the laser system that waste heat generated by the laser system remains less than the determinant amount of waste heat.

40. The laser system of claim 32, wherein the data processing means further supplies the at least one control signal in a transition from the first mode to the second mode so that the output power does not overshoot the high output power during the transition by more than a determinant maximum amount of overshoot.

41. The laser system of claim 32, wherein the data processing means supplies the at least one control signal in the second mode to supply unmodulated pump power.

42. The laser system of claim 32, wherein the data processing means supplies the at least one control signal in the second mode to supply modulated pump power.

43. The laser system of claim 32, further including:
means, mounted with the means for extracting and the data processing means, for supplying measurements of the output power to the data processing means; and
the input means includes means for supplying user input setting a desired low output power and a desired high output power; and
wherein the data processing means supplies the at least one control signal in a characterization mode to determine laser parameters based on pump power versus output power measurements for the first mode and for the second mode, and is responsive to the laser parameters, the desired low output power and the desired high output power to generate the low output power and high output power in the first mode and the second mode, respectively.

44. The laser system of claim 32, wherein the data processing means supplies the at least one control signal in response to the input means to effect a transition from the first mode to the second mode without uncomfortable delay relative to a user's reaction time.

45. A method for operating a laser system including a laser resonator, a laser medium and a non-linear crystal, wherein the non-linear crystal provides conversion of an oscillating mode to a desired output frequency, the laser system also including a controllable means for energizing the laser medium, comprising:
controlling the energizing means in a work mode to supply sufficient power to the laser medium to generate a work mode output beam having a desired power from the laser resonator;
controlling the energizing means in a ready mode to supply sufficient power to the laser medium to thermally stabilize the laser resonator above laser threshold for efficient conversion by the non-linear crystal to generate a ready mode output beam from the laser resonator, wherein average power supplied by the energizing means during the ready mode is less than average power supplied by the energizing means during the work mode;
controlling the energizing means during transitions from the ready mode to the work mode, so that the transitions occur without unacceptably long delay relative to user's reaction time.

46. The method of claim 45, wherein the laser system further includes components sensitive to overshoot of the desired output power of more than a determinant amount, and the step of controlling the energizing means during transitions includes:
preventing overshoot of the desired output power, by more than the determinant amount.

47. The method of claim 45, wherein the laser system further includes a cooling sub-system dissipating up to determinant amount of waste heat into air surrounding the laser system, and the steps of controlling the energizing means in the ready and work modes results in average generation of waste heat of less than the determinant amount.

48. The method of claim 45, wherein the step of controlling the energizing means in the ready mode comprises:
modulating the power supplied to the laser medium to improve conversion efficiency of the non-linear crystal for a given average power.

49. The method of claim 48, wherein the step of oontrolling the energizing means in the work mode comprises:
supplying the non-modulated power to the laser medium and Q-switching the laser resonator to improve conversion efficiency of the non-linear crystal for a given average power.

50. The method of claim 48, wherein the step of controlling the energizing means in the work mode comprises:
modulating the power supplied to the laser medium to improve conversion efficiency of the non-linear crystal for a given average power, without Q-switching the laser resonator.

51. The method of claim 48, wherein the step of controlling the energizing means in the work mode comprises:
modulating the power supplied to the laser medium and Q-switching the laser resonator to improve conversion efficiency of the non-linear crystal for a given average power.

52. The method of claim 45, further including:
controlling the energizing means in a standby mode to warm up the energizing means and laser medium without generating an output beam.

53. The method of claim 52, wherein the laser system further includes a cooling sub-system dissipating up to a determinant amount of waste heat into air surrounding the laser system, and the steps of controlling the energizing means in the standby, ready and work modes results in average generation of waste heat of less than the determinant amount.

54. The amount of claim 45, further including:
providing an aim beam derived from the output beam of the laser resonator during the ready mode at the desired output frequency.

55. A method for operating a laser system including a laser medium within a laser resonator for generating an output beam, the laser system also including a controllable means for energizing the laser medium and a detector for indicating power of the output beam, the method comprising:
controlling the energizing means in a characterization mode from time to time to characterize power of the output beam relative to power supplied to the energizing means; and
controlling the energizing means in a work mode in response to the characterization to supply sufficient power to the laser medium to generate a work mode output beam having a desired power from the laser resonator.

56. The method of claim 55, wherein the step of controlling the energizing means in a characterization mode includes:
generating parameters indicating expected output power from the laser resonator versus input power to the energizing means; and
the step of controlling the energizing means in a work mode includes:
evaluating the parameters in response to user input to determine a nominal input power function for the energizing means; and
adjusting the nominal input power to the energizing means in response to the detected output power of the laser resonator.

57. The method of claim 55, further including:
storing a characterization log indicating a history of characterizations of the laser system.

58. The method of claim 57, further including:
providing an interface for remote access to the characterization log.

59. A method for operating a laser system including a laser medium within a laser resonator for generating an output beam, the laser system also including a controllable means for energizing the laser medium and a detector for indicating power of the output beam, the method comprising:
controlling the energizing means in a characterization mode from time to time to characterized power of the output beam relative to power supplied to the energizing means for at least first and second energizing modes;
controlling the energizing means in the first energizing mode in response to the characterization for the first energizing mode to supply sufficient power to the laser medium to generate an output beam having first characteristics from the laser resonator; and
controlling the energizing means in the second energizing mode in response to the characterization for the second energizing mode to supply sufficient power to the laser medium to generate an output beam having second characteristics from the laser resonator.

60. The method of claim 59, wherein the step of controlling the energizing means in a characterization mode includes:
generating parameters indicating expected output power from the laser resonator versus input power to the energizing means for the first and second energizing modes; and
the steps of controlling the energizing means in the first and second energizing modes includes:
evaluating the parameters for the respective modes in response to user input to determine a nominal input power function to the energizing means; and
adjusting the nominal input power to the energizing means in response to the detected output power of the laser resonator.

61. The method of claim 59, further including:
storing a characterization log indicating a history of characterizations of the laser system.

62. The method of claim 61, further including:
providing an interface for remote access to the characterization log.

63. A method for operating a laser system, including a laser resonator, a laser medium and a non-linear crystal, for generating an output beam, wherein the non-linear crystal, crystal provides conversion of an oscillating mode to a desired output frequency, the laser system also including a controllable means for energizing the laser medium and a detector for indicating power of the output beam, comprising:
controlling the energizing means in a characterization mode from time to time to characterize power of the output beam relative to power supplied to the energizing means for at least a work mode and a ready mode;
controlling the energizing means in the work mode in response to the characterization for the work mode to supply sufficient power to the laser medium to generate a work mode output beam having a desired power from the laser resonator; and
controlling the energizing means in the ready mode in response to the characterization for the ready mode to supply sufficient power to the laser medium to thermally stabilize the laser resonator above laser threshold for efficient conversion by the non-linear crystal to generate a ready mode output beam from the laser resonator, wherein average power supplied by the energizing means during the ready mode is less than average power supplied by the energizing means during the work mode.

64. The method of claim 63, wherein the step of controlling the energizing means in a characterization mode includes:
generating parameters indicating expected output power from the laser resonator versus input power to the energizing means for the work and ready modes; and
the steps of controlling the energizing means in the work and ready modes includes:
evaluating the parameters for the respective work and ready modes in response to user input to determine a nominal input power function for the energizing means; and
adjusting the nominal input power function for the energizing means in response to the detected output power of the laser resonator.

65. The method of claim 63, further including:
controlling the energizing means in response to the characterizations for the ready and work modes during transitions from the ready mode to the work mode, so that the transitions occur without unacceptably long delay relative to user's reaction time.

66. The method of claim 63, wherein the laser system further includes components sensitive to overshoot of the desired output power of more than a determinant amount, and further including:
controlling the energizing means in response to the characterizations for the ready and work modes during transitions from the ready mode to the work mode, to prevent overshoot of the desired output power, by more than the determinant amount.

67. The method of claim 63, wherein the step of controlling the energizing means in the ready mode comprises:
modulating the power supplied to the laser medium to improve conversion efficiency of the non-linear crystal for a given average power.

68. The method of claim 67, wherein the step of controlling the energizing means in the work mode comprises:
supplying the non-modulated power to the laser medium and Q-switching the laser resonator to improve conversion efficiency of the non-linear crystal for a given average power.

69. The method of claim 67, wherein the step of controlling the energizing means in the work mode comprises:
modulating the power supplied to the laser medium to improve conversion efficiency of the non-linear crystal for a given average power, without Q-switching the laser resonator.

70. The method of claim 67, wherein the step of controlling the energizing means in the work mode comprises:
modulating the power supplied to the laser medium and Q-switching the laser resonator to improve conversion efficiency of the non-linear crystal for a given average power.

71. The method of claim 63, further including:
controlling the energizing means in a standby mode to warm up the energizing means and laser medium without generating an output beam.

72. The method of claim 63, further including:
storing a characterization log indicating a history of characterizations of the laser system.

73. The method of claim 72, further including:
providing an interface for remote access to the characterization log.

74. An apparatus for controlling a laser system including a laser medium within a laser resonator for generating an output beam, the laser system also including a controllable means for energizing the laser medium and a detector for indicating power of the output beam, the apparatus comprising:
means coupled with the energizing means and the detector, for controlling the energizing means in a characterization mode to characterize power of the output beam relative to power supplied to the energizing means; and
means, coupled with the energizing means and the detector, for controlling the energizing means in a work mode in response to the characterization to supply sufficient power to the laser medium to generate a work mode output beam having a desired power from the laser resonator.

75. The apparatus of claim 74, wherein the means for controlling the energizing means in a characterization mode includes:
means for generating parameters indicating expected output power from the laser resonator versus input power to the energizing means; and
the means for controlling the energizing means in a work mode includes:
means for evaluating the parameters in response to user input to determine a nominal input power function for the energizing means; and
means for adjusting the nominal input power to the energizing means in response to the detected output power of the laser resonator.

76. The apparatus of claim 74, further including:
means, responsive to user input, for enabling the means for controlling the energizing means in a characterization mode whereby a user may from time to time cause automatic re-characterization of the laser system to account for changing characteristics of elements of the laser system over time.

77. The apparatus of claim 74, further including:
means, responsive to turning on the laser system, for enabling the means for controlling the energizing means in a characterization mode whereby automative recharacterization of the laser system to account for changing characteristics of elements of the laser system over time is accomplished when the laser system is turned on.

78. The apparatus of claim 74, further including:
means for sensing an environmental condition affecting the laser system; and
means, responsive to means for sensing and coupled with the means for controlling the laser system in a characterization mode, for enabling the means for controlling the energizing means in a characterization mode whereby changes in the environmental condition from tim e to time cause automatic re-characterization of the laser system.

79. The apparatus of claim 74, further including:
means for storing a characterization log indicating a history of characterizations of the laser system.

80. The apparatus of claim 79, further including:
an interface for remote access to the characterization log.

81. An apparatus for controlling a laser system including a laser medium within a laser resonator for generating an output beam, the laser system also including a controllable means for energizing the laser medium and a detector for indicating power of the output beam, the apparatus comprising:

- means, coupled with the energizing means and the detector, for controlling the energizing means in a characterization mode to store a characterization of power of the output beam relative to power supplied to the energizing means for at least first and second energizing modes;
- means, coupled with the energizing means and the detector, for controlling the energizing means in the first energizing mode in response to the stored characterization for the first energizing mode to supply sufficient power to the laser medium to generate an output beam having first characteristics from the laser resonator; and
- means, coupled with the energizing means and the detector, for controlling the energizing means in the second energizing mode in response to the stored characterization for the second energizing mode to supply sufficient power to the laser medium to generate an output beam having second characteristics from the laser resonator.

82. The apparatus of claim 81, wherein the means for controlling the energizing means in a characterization mode includes:
- means for generating parameters indicating expected output power from the laser resonator versus input power to the energizing means for the first and second energizing modes; and
- the means for controlling the energizing means in the first and second energizing modes includes:
- means for evaluating the parameters for the respective modes in response to user input to determine a nominal input power function for the energizing means; and
- means for adjusting the nominal input power function to the energizing means in response to the detected output power of the laser resonator.

83. The apparatus of claim 81, further including:
- means, responsive to user input, for enabling the means for oontrolling the energizing means in a characterization mode whereby a user may from time to time cause automatic re-characterization of the laser system to account for changing characteristics of elements of the laser system over time.

84. The apparatus of claim 81, further including:
- means for sensing an environmental condition affecting the laser system; and
- means, responsive to means for sensing and coupled with the means for controlling the laser system in a characterization mode, for enabling the means for controlling the energizing means in a characterization mode whereby changes in the environmental condition from time to time cause automatic re-characterization of the laser system.

85. The apparatus of claim 81, further including:
- means, responsive to turning on the laser system, for enabling the means for controlling the energizing means in a characterization mode whereby automatic re-characterization of the laser system to account for changing characteristics of elements of the laser system over time is accomplished when the laser system is turned on.

86. The apparatus of claim 81, further including:
- means for storing a characterization log indicating a history of characterizations of the laser system.

87. The apparatus of claim 86, further including:
- an interface for remote access to the characterization log.

88. An apparatus for controlling a laser system, including a laser resonator, a laser medium and a non-linear crystal, for generating an output beam, wherein the non-linear crystal provides conversion of an oscillating mode to a desired output frequency, the laser system also including a controllable means for energizing the laser medium and a detector for indicating power of the output beam, comprising:

- means, coupled with the energizing means and the detector, for controlling the energizing means in a characterization mode to store a characterization of power of the output beam relative to power supplied to the energizing means for at least a work mode and a ready mode;
- means, coupled with the energizing means and the detector, for controlling the energizing means in the work mode in response to the stored characterization for the work mode to supply sufficient power to the laser medium to generate a work mode output beam having a desired power from the laser resonator; and
- means, coupled with the energizing means and the detector, for oontrolling the energizing means in the ready mode in response to the stored characterization for the ready mode to supply sufficient power to the laser medium to thermally stabilize the laser resonator above laser threshold for efficient conversion by the non-linear crystal to generate a ready mode output beam from the laser resonator, wherein average power supplied by the energizing means during the ready mode is less than average power supplied by the energizing means during the work mode.

89. The apparatus of claim 88, wherein the means for oontrolling the energizing means in a characterization mode includes:
- means for generating parameters indicating expected output power from the laser resonator versus input power to the energizing means for the work and ready modes; and
- the means for controlling the energizing means in the work and ready modes includes:
- means for evaluating the parameters for the respective work and ready modes in response to user input to determine a nominal input power function for the energizing means; and
- means for adjusting the nominal input power function for the energizing means in response to the detected output power of the laser resonator.

90. The apparatus of claim 88, further including:
- means, coupled with the energizing means and the detector, for controlling the energizing means in response to the stored characterizations for the ready and work modes during transitions from the ready mode to the work mode, so that the transitions occur without unacceptably long delay relative to user's reaction time.

91. The apparatus of claim 88, wherein the laser system further includes components sensitive to overshoot of the desired output power of more than a determinant amount, and further including:
- means, coupled with the energizing means and the detector, for controlling the energizing means in response to the stored characterizations for the ready and work modes during transitions from the ready mode to the work mode, to prevent overshoot of the desired output power, by more than the determinant amount.

92. The apparatus of claim 88, wherein the means for controlling the energizing means in the ready mode comprises:
means for modulating the power supplied to the laser medium to improve conversion efficiency of the non-linear crystal for a given average power.

93. The apparatus of claim 92, wherein the means for controlling the energizing means in the work mode comprises:
means for supplying non-modulated power to the laser medium and Q-switching the laser resonator to improve conversion efficiency of the non-linear crystal for a given average power.

94. The apparatus of claim 92, wherein the means for controlling the energizing means in the work mode comprises:
means for modulating the power supplied to the laser medium to improve conversion efficiency of the non-linear crystal for a given average power, without Q-switching the laser resonator.

95. The apparatus of claim 92, wherein the means for controlling the energizing means in the work mode comprises:
means for modulating the power supplied to the laser medium and Q-switching the laser resonator to improve conversion efficiency of the non-linear crystal for a given average power.

96. The apparatus of claim 88, further including:
means, coupled with the energizing means and the detector, for controlling the energizing means in a standby mode to warm up the energizing means and laser medium without generating an output beam.

97. The apparatus of claim 88, further including:
means, responsive to user input, for enabling the means for controlling the energizing means in a characterization mode whereby a user may from time to time cause automatic re-characterization of the laser system to account for changing characteristics of elements of the laser system over time.

98. The apparatus of claim 88, further including:
means, responsive to turning on the laser system, for enabling the means for controlling the energizing means in a characterization mode whereby automatic re-characterization of the laser system to account for changing characteristics of elements of the laser system over time is accomplished when the laser system is turned on.

99. The apparatus of claim 88, further including:
means for sensing an environmental condition affecting the laser system; and
means, responsive to means for sensing and coupled with the means for controlling the laser system in a characterization mode, for enabling the means for controlling the energizing means in a characterization mode whereby changes in the environmental condition from time to time cause automatic re-characterization of the laser system.

100. The apparatus of claim 88, further including:
means for storing a characterization log indicating a history of characterizations of the laser system.

101. The apparatus of claim 100, further including:
an interface for remote access to the characterization log.

* * * * *